US012109328B2

(12) United States Patent
Park

(10) Patent No.: US 12,109,328 B2
(45) Date of Patent: Oct. 8, 2024

(54) MEDICAL IMPLANTS INCLUDING NEGATIVE POISSON'S RATIO MATERIALS

(71) Applicant: Joon Bu Park, Las Vegas, NV (US)

(72) Inventor: Joon Bu Park, Las Vegas, NV (US)

( * ) Notice: Subject to any disclaimer, the term of this patent is extended or adjusted under 35 U.S.C. 154(b) by 124 days.

(21) Appl. No.: 17/369,756

(22) Filed: Jul. 7, 2021

(65) Prior Publication Data
US 2023/0008452 A1    Jan. 12, 2023

(51) Int. Cl.
| | |
|---|---|
| A61F 2/28 | (2006.01) |
| A61F 2/32 | (2006.01) |
| A61F 2/34 | (2006.01) |
| A61F 2/36 | (2006.01) |
| A61L 27/16 | (2006.01) |
| A61L 27/34 | (2006.01) |
| A61L 27/50 | (2006.01) |
| A61L 27/56 | (2006.01) |
| C08J 7/04 | (2020.01) |
| A61B 17/80 | (2006.01) |

(Continued)

(52) U.S. Cl.
CPC .............. *A61L 27/50* (2013.01); *A61F 2/34* (2013.01); *A61F 2/36* (2013.01); *A61F 2/3662* (2013.01); *A61L 27/165* (2013.01); *A61L 27/34* (2013.01); *A61L 27/56* (2013.01); *C08J 7/0427* (2020.01); *A61B 17/80* (2013.01); *A61F 2002/3093* (2013.01); *A61F 2002/30971* (2013.01); *A61F 2/4241* (2013.01); *A61L 2430/12* (2013.01); *C08J 2323/06* (2013.01); *C08J 2333/12* (2013.01)

(58) Field of Classification Search
CPC .. A61F 2/34; A61F 2/36; A61F 2/3662; A61F 2002/30971; A61F 2002/3093; A61F 2002/30878; A61F 2310/00952; A61L 27/165; A61L 27/34; A61L 27/50; A61L 27/56; C08J 7/0427; C08J 2323/06; C08J 2333/12; C09D 133/12
See application file for complete search history.

(56) References Cited

U.S. PATENT DOCUMENTS

| 4,491,987 A | 1/1985 | Park |
|---|---|---|
| 5,004,476 A | 4/1991 | Cook |

(Continued)

FOREIGN PATENT DOCUMENTS

| EP | 3466372 | 7/2020 |
|---|---|---|
| GB | 2495272 | 6/2016 |

(Continued)

OTHER PUBLICATIONS

Minary-Jolandan et al., "Uncovering Nanoscale Electromechanical Heterogeneity in the Subfibrillar Structure of Collagen Fibrils Responsible for the Piezoelectricity of Bone," ACS Nano, Jun. 2009, 3(7): 1859-1863.

(Continued)

*Primary Examiner* — Dinah Baria
(74) *Attorney, Agent, or Firm* — Fish & Richardson P.C.

(57) ABSTRACT

A medical implant includes a first implant body and a pre-coating covering at least a portion of an outer surface of the first implant body. The pre-coating has a negative Poisson's ratio. A method of making a medical implant includes applying a precursor material on a surface of a first implant body, the first implant body having a positive Poisson's ratio. A stimulus is applied to the precursor material, the stimulus causing the precursor material to form a coating having a negative Poisson's ratio

17 Claims, 21 Drawing Sheets

(51) Int. Cl.
    *A61F 2/30*     (2006.01)
    *A61F 2/42*     (2006.01)

(56) References Cited

U.S. PATENT DOCUMENTS

| | | |
|---|---|---|
| 5,035,713 A | 7/1991 | Friis |
| 5,343,877 A | 9/1994 | Park |
| 6,312,473 B1 | 11/2001 | Oshida |
| 6,558,428 B2 | 5/2003 | Park |
| 6,749,639 B2 | 6/2004 | Lewallen |
| 9,241,808 B2 | 1/2016 | Sabatino |
| 10,994,057 B2 | 5/2021 | Williams et al. |
| 2014/0114260 A1 | 4/2014 | Kawakatsu et al. |
| 2015/0133593 A1 | 5/2015 | Kissell et al. |
| 2021/0113356 A1 | 4/2021 | Laszczak et al. |

FOREIGN PATENT DOCUMENTS

| | | |
|---|---|---|
| WO | WO 2020/072515 | 4/2020 |
| WO | WO 2021/042044 | 3/2021 |

OTHER PUBLICATIONS

Park et al., "Piezoelectric ceramic implants: A feasibility study," Journal of Biomedical Materials Research, May 1980, 14(3): 269-277.
Park et al., "Piezoelectric ceramic implants: in vivo results," Journal of Biomedical Materials Research, Jan. 1981, 15(1): 103-110.
Zhang et al., "Aligned porous barium titanate/hydroxyapatite composites with high piezoelectric coefficients for bone tissue engineering," Materials Science and Engineering: C, Jun. 2014, 39: 143-149.
International Search Report and Written Opinion in International Appl. No. PCT/US2022/036310, dated Nov. 16, 2022, 9 pages.
International Preliminary Report on Patentability in International Appln. No. PCT/US2022/036310, mailed on Jan. 18, 2024, 7 pages.

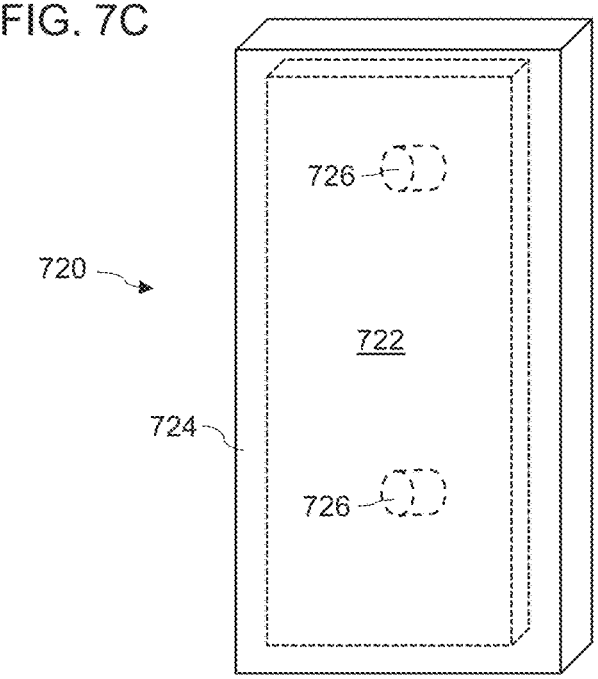
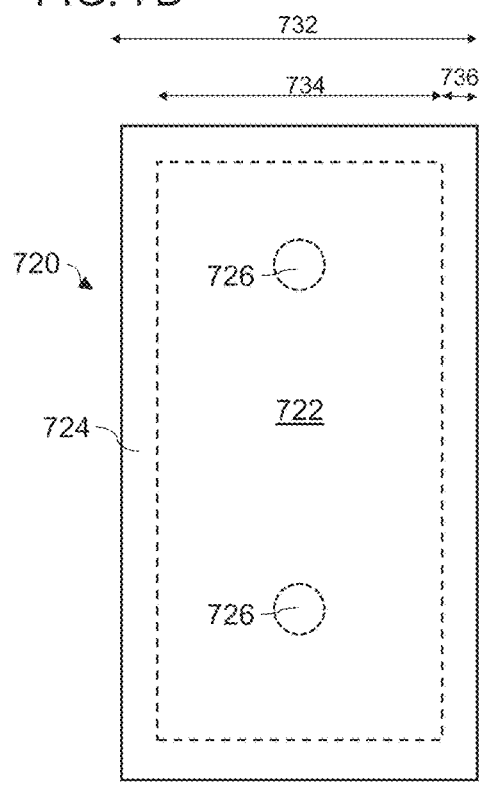
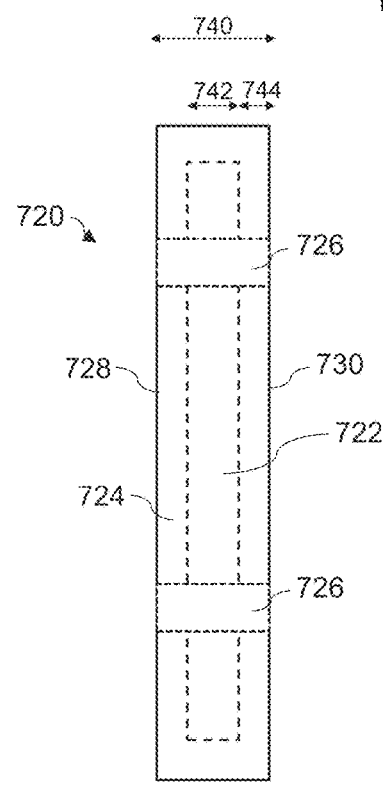

+ Foaming Agent

1000

1004  1002

Heat/Pressure

1006

Screwhole formation

Heat/Pressure

Remove oxide

Coat with precursor material

Heat/Pressure

Apply porous adhesive

Heat/Pressure

MEDICAL IMPLANTS INCLUDING NEGATIVE POISSON'S RATIO MATERIALS

BACKGROUND

The present disclosure relates generally to materials for and construction of various types of medical implants, including joint prostheses and bone plates.

Medical implants can be integrated into patients' bodies for various purposes, including replacing a missing biological structure, supporting a damaged biological structure, or enhancing an existing biological structure.

SUMMARY

We describe here medical implants, such as joint prostheses, limb prostheses, and bone plates, that include materials having a negative Poisson's ratio ("NPR materials"). For instance, an inner portion of a bone plate can include an NPR material that reduces implant weight and improves stress characteristics of the bone plate. In some cases, an outer portion of a medical implant, such as a hip prosthesis, can be formed of an NPR material. Other arrangements on NPR material included in medical implants are also described. Medical implants including an NPR material may expand less than equivalent implants formed of a positive Poisson's ratio material ("PPR material"), which can reduce wear and strain in implants over time. The use of NPR materials can help maintain homeostasis and promote more healthy bone growth and healing.

In one aspect, this disclosure describes a medical implant. The medical implant includes a first implant body and a pre-coating covering at least a portion of an outer surface of the first implant body. The pre-coating has a negative Poisson's ratio.

This medical implant, and at least some other medical implants described herein, may include any one or more of at least the following features.

In some implementations, the first implant body includes at least a portion having a positive Poisson's ratio. In some implementations, the first implant body includes an inner cup of an acetabular cup. In some implementations, the inner cup includes ultra-high-molecular-weight polyethylene. In some implementations, the first implant body includes a prosthetic femoral stem. In some implementations, the pre-coating includes polymethyl methacrylate having a negative Poisson's ratio. In some implementations, the pre-coating includes a bone ingrowth-promoting material having a negative Poisson's ratio. In some implementations, the pre-coating has a thickness between 1 mm and 5 mm. In some implementations, the pre-coating adheres more strongly to a bone cement than does the first implant body. In some implementations, the bone cement includes polymethyl methacrylate.

In an aspect, this disclosure describes a method of making a medical implant. The method includes applying a precursor material on a surface of a first implant body, the first implant body having a positive Poisson's ratio. The method includes applying a stimulus to the precursor material, the stimulus causing the precursor material to form a coating having a negative Poisson's ratio.

This method, and at least some other methods described herein, may include any one or more of at least the following features.

In some implementations, the stimulus comprises at least one of heat or pressure. In some implementations, the method includes, prior to applying the precursor material, removing an oxide layer from the surface of the first implant body. In some implementations, the coating has a thickness between 1 mm and 5 mm. In some implementations, the first implant body includes an inner cup of an acetabular cup. In some implementations, the first implant body includes a prosthetic femoral stem. In some implementations, the precursor material includes a porous foam. In some implementations, the coating includes polymethyl methacrylate having a negative Poisson's ratio. In some implementations, the coating includes a bone ingrowth-promoting material having a negative Poisson's ratio. In some implementations, the coating adheres more strongly to a bone cement than does the first implant body.

In an aspect, this disclosure describes a medical implant. The medical implant includes an internal region having a negative Poisson's ratio, and an outer region at least partially surrounding the internal region, the outer region having a positive Poisson's ratio.

This medical implant, and at least some other medical implants described herein, may include any one or more of at least the following features.

In some implementations, the internal region comprises steel having a negative Poisson's ratio. In some implementations, the internal region at least partially defines one or more screw holes extending through the medical implant. In some implementations, the medical implant includes a bone plate. In some implementations, the internal region is arranged to contact a bone screw inserted through the bone plate.

In an aspect, this disclosure describes a method of making a medical implant. The method includes forming an internal implant body including a precursor material, applying a stimulus to the precursor material, the stimulus causing the precursor material to have a negative Poisson's ratio, and forming an outer implant body at least partially surrounding the internal implant body, the outer implant body having a positive Poisson's ratio.

This method, and at least some other methods described herein, may include any one or more of at least the following features.

In some implementations, the stimulus includes at least one of heat or pressure. In some implementations, the precursor material includes a porous foam. In some implementations, the porous foam includes a porous steel foam. In some implementations, the method includes forming one or more screw holes extending through the medical implant, including through the internal implant body. In some implementations, the method includes applying the stimulus subsequent to forming the outer implant body at least partially surrounding the internal implant body.

In an aspect, this disclosure describes a medical implant. The medical implant includes a grommet. The grommet includes a negative Poisson's ratio material.

This medical implant, and at least some other medical implants described herein, may include any one or more of at least the following features.

In some implementations, the grommet defines an aperture configured to receive a bone screw. In some implementations, the aperture has a diameter between 1.5 mm and 6.5 mm. In some implementations, the negative Poisson's ratio material includes stainless steel. In some implementations, the negative Poisson's ratio material includes a titanium-containing metal. In some implementations, the titanium-containing metal includes $Ti_6Al_4V$. In some implementations, the grommet is configured to be placed between a stem of a finger joint prosthesis and a bone to which the finger joint prosthesis is affixed. In some implementations, the grommet is configured to be placed between a bone screw and a bone in which the bone screw is inserted. In some implementations, the negative Poisson's ratio material includes at least one of stainless steel or a titanium-containing metal.

In an aspect, this disclosure describes a medical implant. The medical implant includes biocompatible polymer fibers, and a negative Poisson's ratio material in which the biocompatible polymer fibers are embedded.

This medical implant, and at least some other medical implants described herein, may include any one or more of at least the following features.

In some implementations, the biocompatible polymer fibers include at least one of polyethylene, polypropylene, polytetrafluoroethylene, or a nylon. In some implementations, the medical implant comprises a finger joint prosthetic. In some implementations, the negative Poisson's ratio material comprises silicone.

In an aspect, this disclosure describes a method of making a medical implant. The method includes binding together biocompatible polymer fibers in a porous adhesive, and applying a stimulus to the porous adhesive, the stimulus causing the porous adhesive to have a negative Poisson's ratio.

This method, and at least some other methods described herein, may include any one or more of at least the following features.

In some implementations, binding together the biocompatible polymer fibers in the porous adhesive includes applying the porous adhesive to the biocompatible polymer fibers in a mold. In some implementations, the biocompatible polymer fibers include at least one of polyethylene, polypropylene, polytetrafluoroethylene, or a nylon. In some implementations, the method includes, subsequent to applying the stimulus, repeatedly stretching the porous adhesive having the negative Poisson's ratio. In some implementations, repeatedly stretching the porous adhesive is performed in an inert atmosphere. In some implementations, the stimulus includes at least one of heat or pressure.

In an aspect, this disclosure describes a medical implant. The medical implant includes a bone plate. The bone plate includes a negative Poisson's ratio material.

This medical implant, and at least some other medical implants described herein, may include any one or more of at least the following features.

In some implementations, the negative Poisson's ratio material is embedded in a positive Poisson's ratio material of the bone plate. In some implementations, the bone plate defines a screw hole configured to receive a bone screw, and the negative Poisson's ratio material is arranged to contact the bone screw when the bone screw is positioned through the screw hole. In some implementations, the negative Poisson's ratio material is arranged between the bone screw and a positive Poisson's ratio material included in the bone plate.

In an aspect, this disclosure describes a joint prosthesis. The joint prosthesis includes a body including two stems and a hinge joining the two stems. The joint prosthesis includes a grommet configured to be placed between the body and a bone to which the body is affixed. At least one of the grommet or the two stems comprises a negative Poisson's ratio material.

This joint prosthesis, and at least some other joint prostheses described herein, may include any one or more of at least the following features.

In some implementations, each stem of the two stems includes biocompatible polymer fibers bound by the negative Poisson's ratio material. In some implementations, the grommet includes the negative Poisson's ratio material. In some implementations, the negative Poisson's ratio material includes a titanium-containing metal. In some implementations, the joint prosthesis includes a finger joint prosthesis.

In an aspect, this disclosure describes a dental implant. The dental implant includes a negative Poisson's ratio material defining an open cavity. The open cavity is configured to receive an abutment.

This dental implant, and at least some other dental implants described herein, may include any one or more of at least the following features.

In some implementations, the dental implant includes a prosthetic tooth in which the negative Poisson's ratio material is included. In some implementations, the dental implant includes a fixture in which the negative Poisson's ratio material is included. In some implementations, the dental implant includes a positive Poisson's ratio material partially enclosing the negative Poisson's ratio material.

Other implementations are also within the scope of the claims.

DESCRIPTION OF DRAWINGS

FIGS. 7A-7E are diagrams and cross-section views of example bone plates.

DETAILED DESCRIPTION

We describe here medical implants, such as prostheses, that are formed of materials having a negative Poisson's ratio ("NPR materials," also referred to as auxetic materials). For instance, an inner portion, outer portion, or all of a prosthetic can be formed of an NPR material. This composition can facilitate reduced weight, improved joint and fixation reliability, and improved stress and strain characteristics over time.

Figure 1:
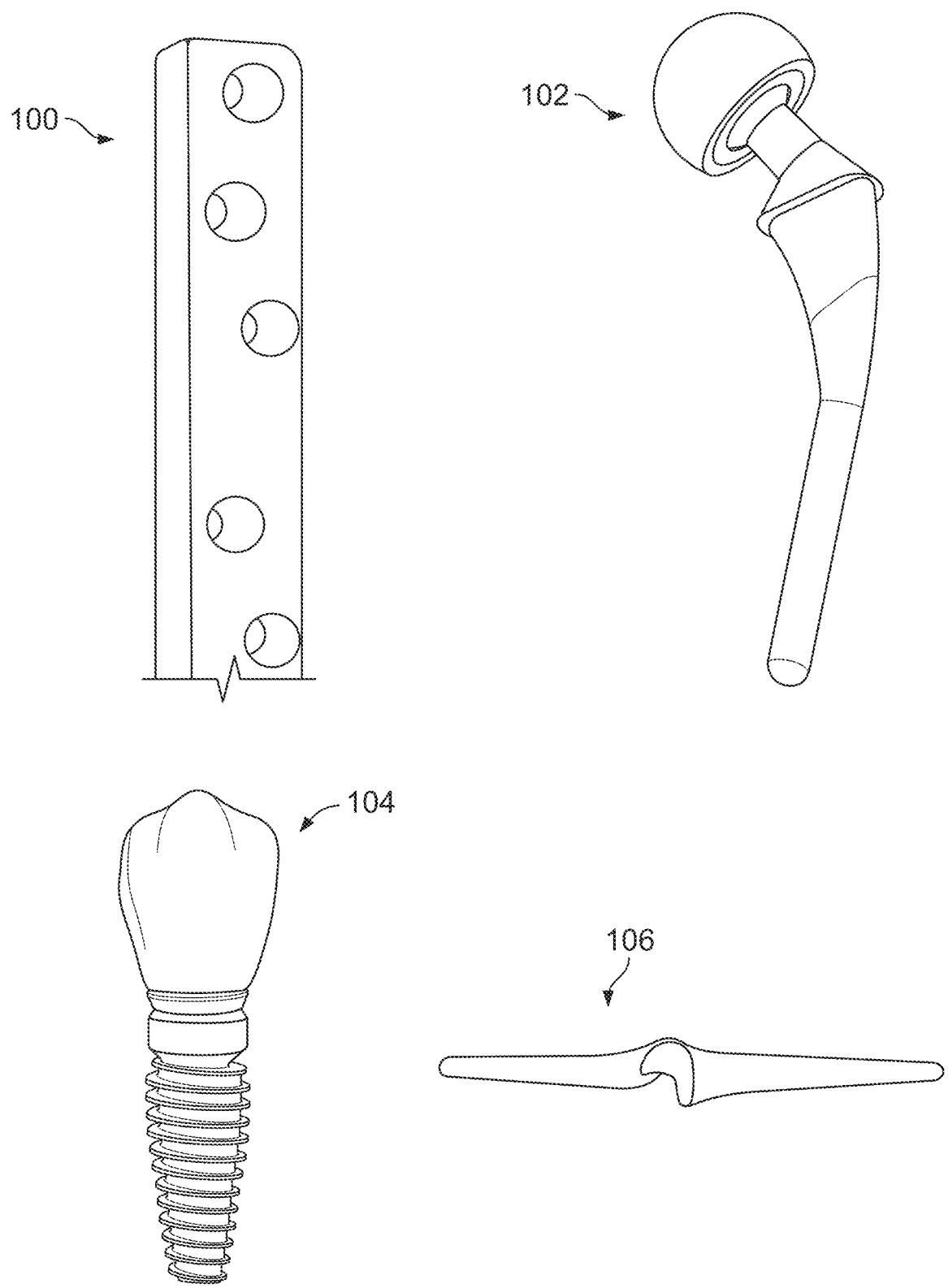
FIG. 1 is a diagram of several example medical implants.

Referring to FIG. 1, several types of medical implants are shown, including a bone plate 100, a hip joint prosthesis 102, a dental implant 104, and a finger joint prosthesis 106.

These medical implants are non-limiting examples of the types, shapes, and sizes of medical implants into which the NPR materials described here can be integrated.

Figure 2:
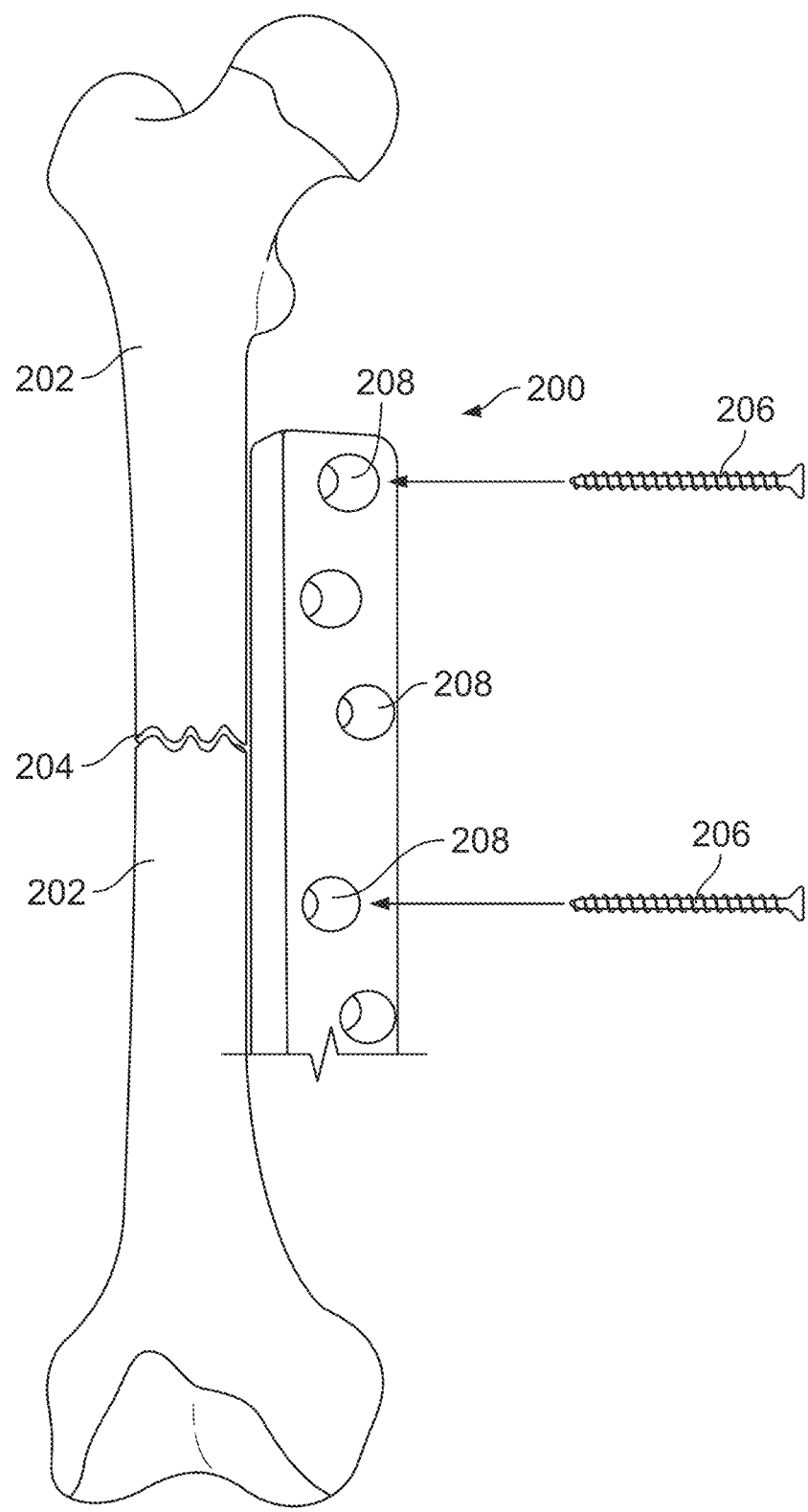
FIG. 2 is a diagram of an example bone plate.

Bone plates (sometimes referred to as fixation plates, fracture plates, or orthopedic plates), such as the bone plate 100, are affixed to bones, either permanently or during a healing process. For example, as shown in FIG. 2, a bone plate 200 may hold two pieces of bone 202 in alignment with another while a fracture 204 heals. The bone plate 200 is affixed to the bone 202 by bone screws 206 inserted through screw holes 208, where stress is often concentrated.

Figure 3:
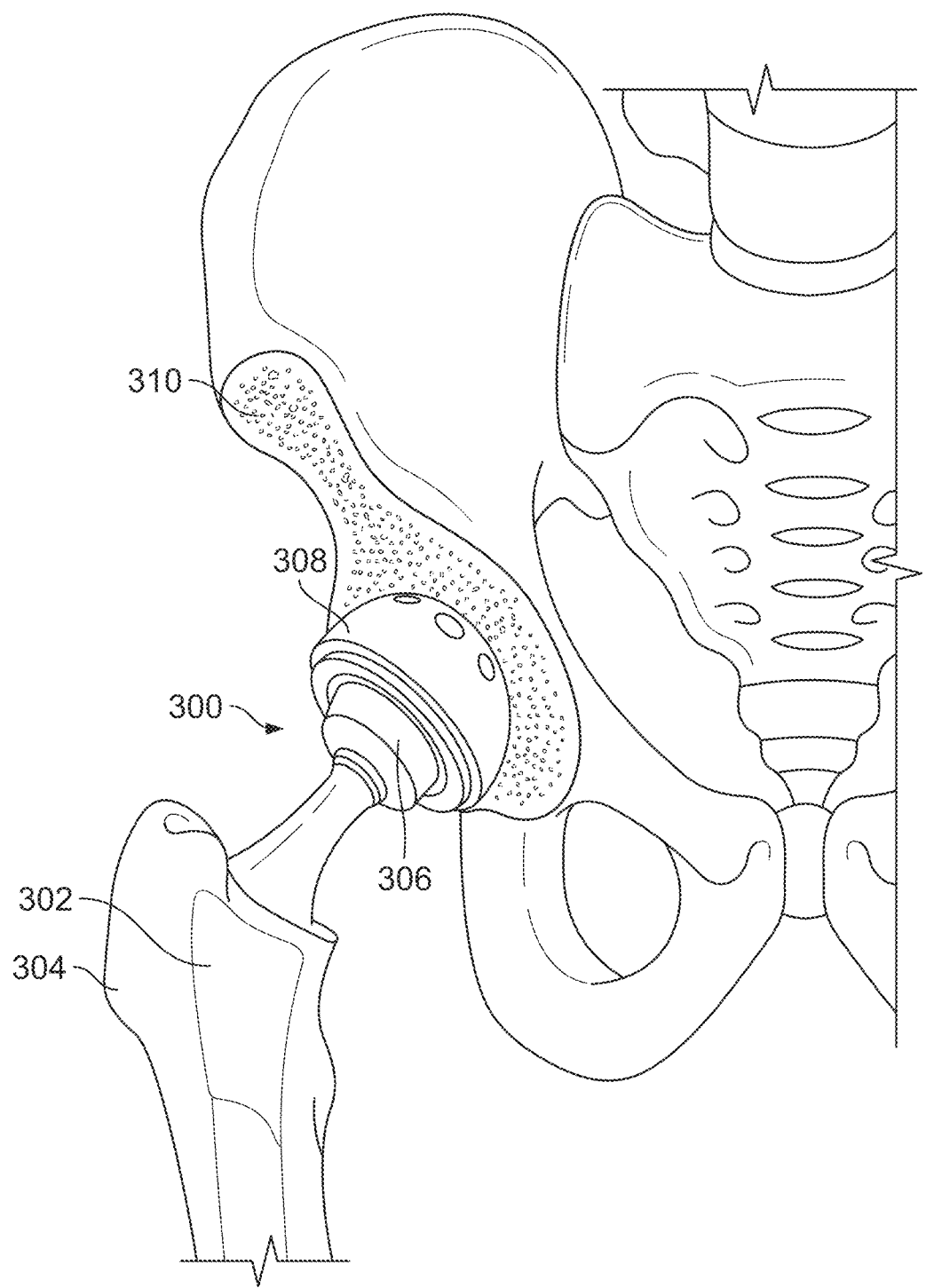
FIG. 3 is a diagram of an example prosthetic hip.

As shown in FIG. 3, a typical full hip prosthesis 300 includes three primary components. A stem 302 is inserted into the femur 304. A ball 306 (sometimes referred to as a femoral head component) is attached to the stem 302 and has freedom of movement within an acetabular cup 308 implanted within the pelvis 310. In some cases, only some of these components are used. For example, in a partial hip replacement, the femoral head is replaced by an artificial femoral head component, without use of an artificial acetabular cup or stem 302.

Figure 4:
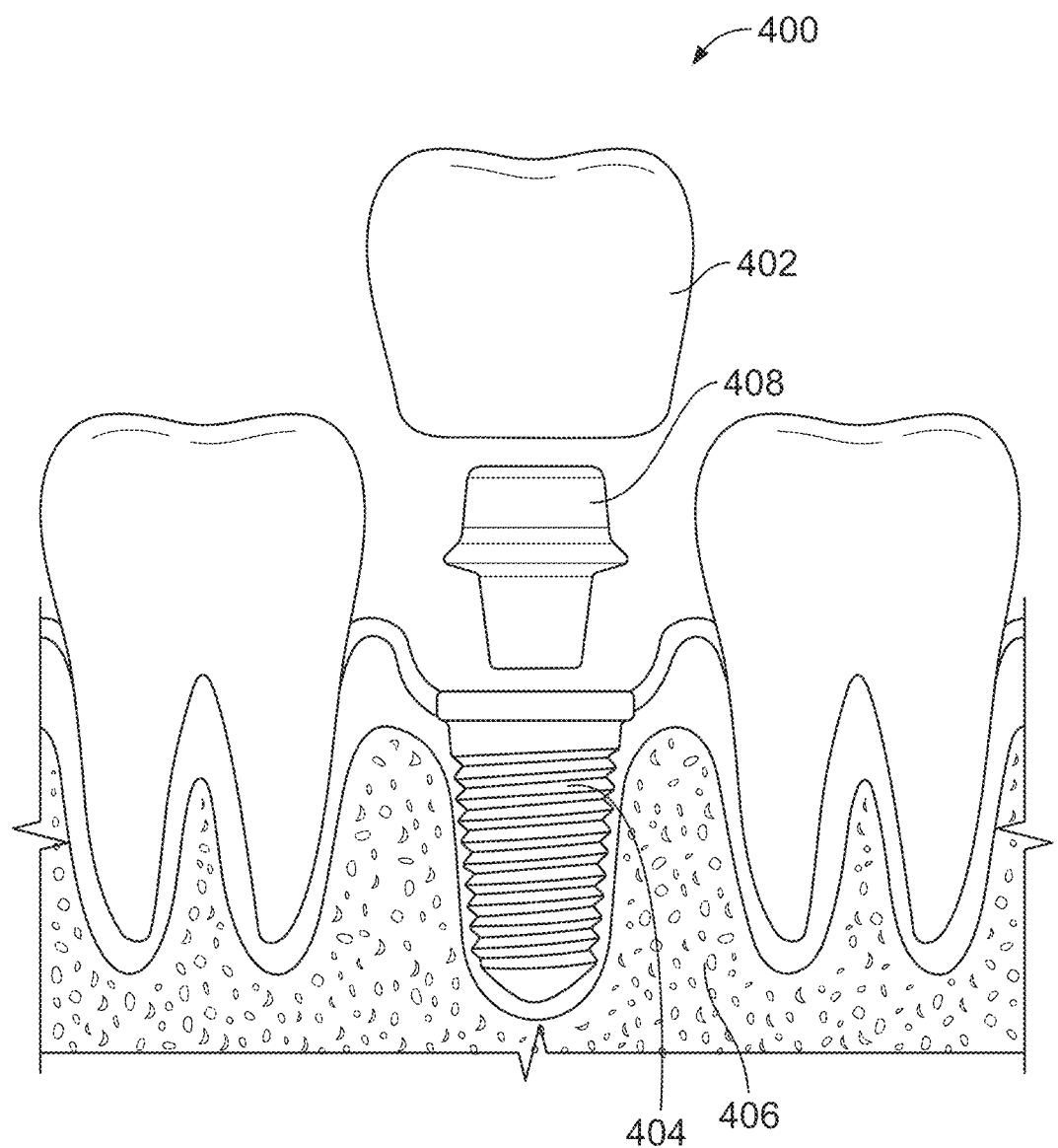
FIG. 4 is a diagram of an example dental implant.

As shown in FIG. 4, a typical dental implant 400 includes a prosthetic tooth 402, a fixture 404 implanted in bone 406, and an abutment 408 that joins the prosthetic tooth 402 to the fixture 404.

Figure 5:
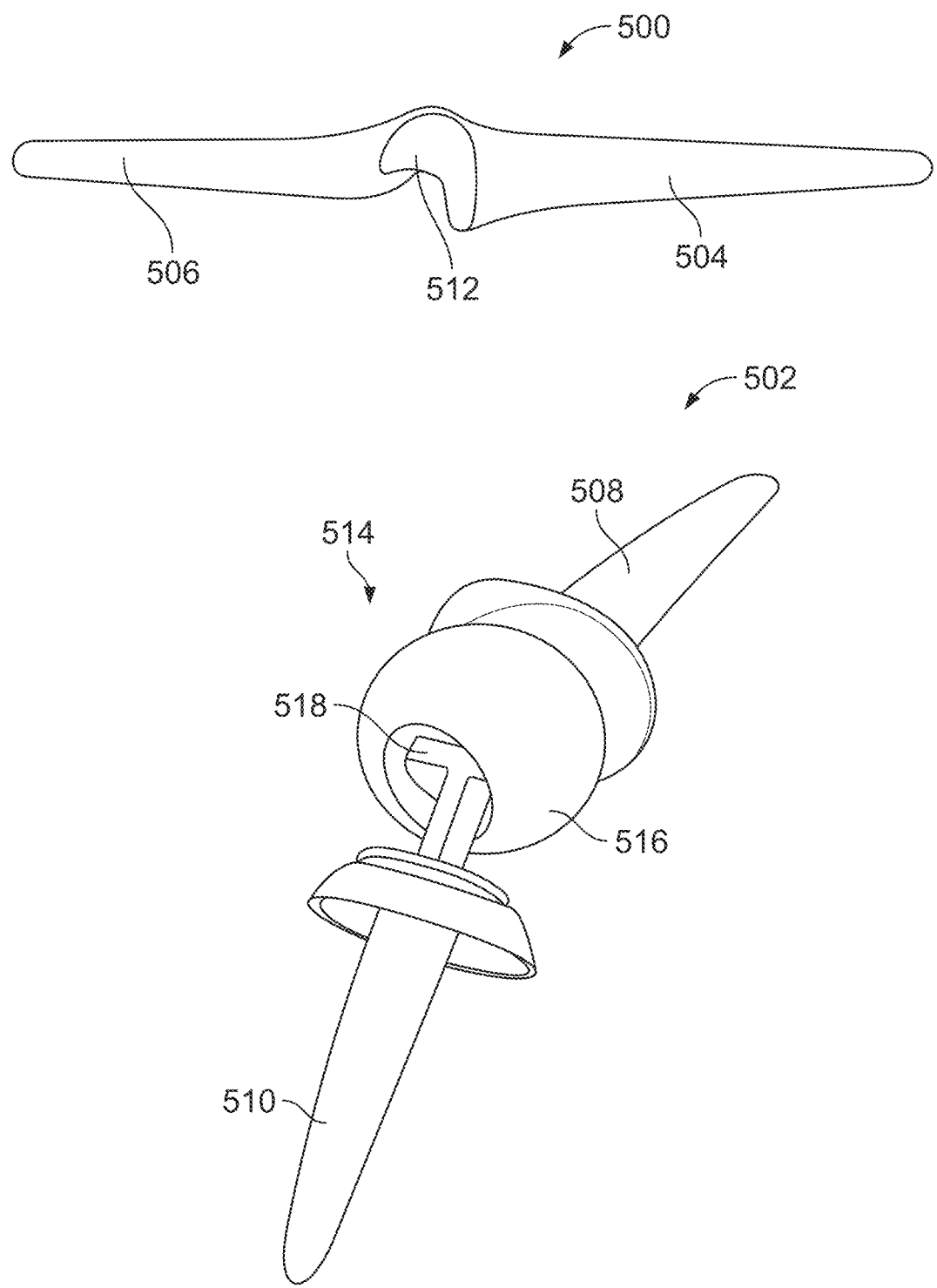
FIG. 5 is a diagram of two example prosthetic finger joints.

As shown in FIG. 5, finger joint prostheses come in various forms, including Swanson prostheses 500 and Stefee prostheses 502, and are commonly used for proximal interphalangeal joint (PIPJ) and metacarpal interphalangeal joint (MCPJ) replacements. In general, finger joint prostheses include two stems 504, 506, 508, 510 that mate with respective bones on either side of the joint, and a hinge 512, 514 that allows movement of the two stems 504, 506, 508, 510 with respect to one another. The hinge 512, 514 can be integrated together with the stems 504, 506, 508, 510, as in the unibody Swanson prosthesis 500, or can include multiple separable components, such as the ball 516 and insert 518 of the Stefee prosthesis 502.

For bone plates, hip prostheses, dental implants, finger joint prostheses, and other medical implants such as tibia prostheses, artificial knees, and spinal fusion components, a primary challenge is the fixation of the prosthesis to bone. Possible fixation methods include direct interference fits or passive (non-interference) fits; mechanical fixation using bone screws, bolts, nuts, wires, etc.; bone cement interdigitation and other bonding methods; and porous ingrowth fixation, in some cases controlled by electrical or electromagnetic stimulation.

All of these fixation methods are based on strong interfaces between bone and artificial materials. However, because the bone often grows after initial healing or after insertion of the medical implant, it can be difficult to maintain homeostasis at the bone-implant interface. In particular, it is important that an optimal range of stress and strain be maintained at the interface, whether to promote desired bone healing, to prevent corrosion or aggravation of joints and fixtures, to keep the medical implant firmly in its installed position, or for other reasons.

An NPR material is a material that has a Poisson's ratio that is less than zero, such that when the material experiences a positive strain along one axis (e.g., when the material is stretched), the strain in the material along the two perpendicular axes is also positive (e.g., the material expands in cross-section). Conversely, when the material experiences a negative strain along one axis (e.g., when the material is compressed), the strain in the material along a perpendicular axis is also negative (e.g., the material compresses along the perpendicular axis). By contrast, a material with a positive Poisson's ratio (a "PPR material") has a Poisson's ratio that is greater than zero. When a PPR material experiences a positive strain along one axis (e.g., when the material is stretched), the strain in the material along the two perpendicular axes is negative (e.g., the material compresses in cross-section), and vice versa.

Figure 6:
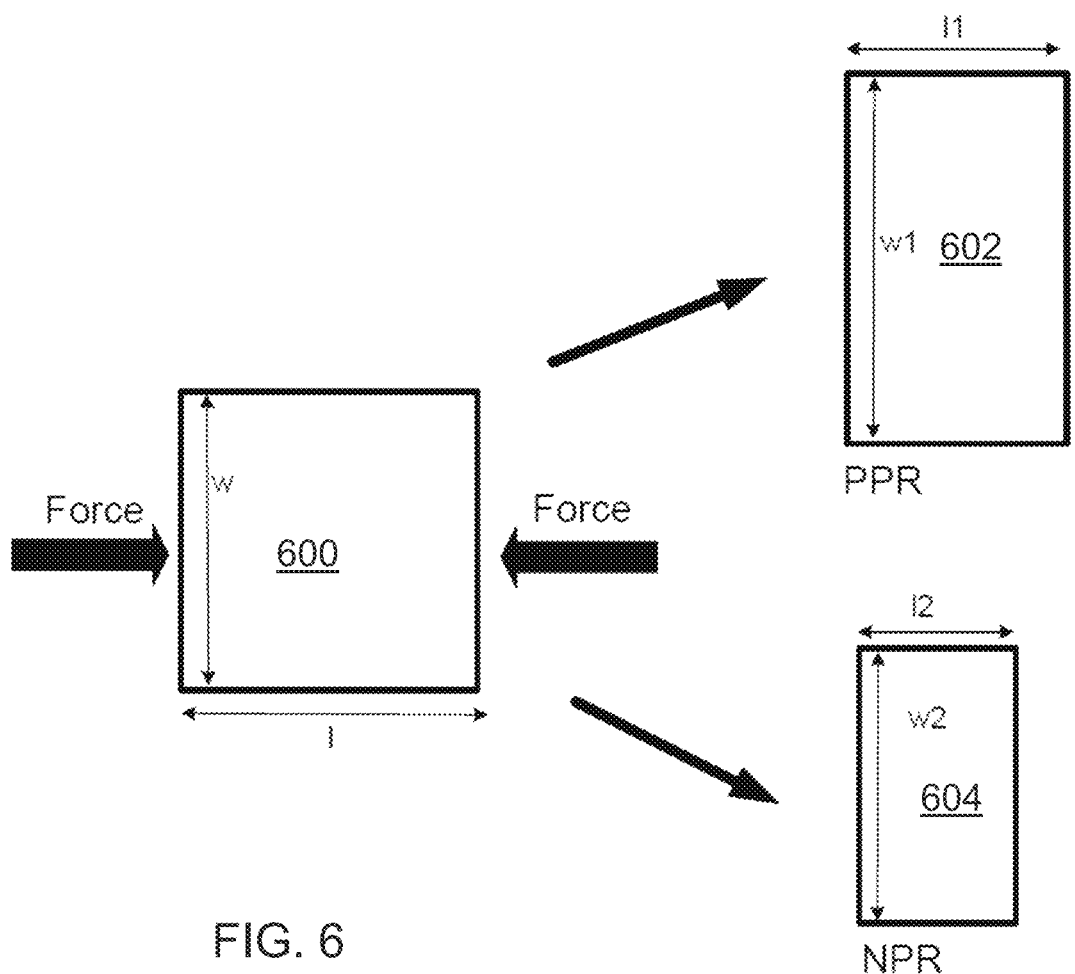
FIG. 6 is an illustration of materials with negative and positive Poisson's ratios.

Materials with negative and positive Poisson's ratios are illustrated in FIG. 6, which depicts a hypothetical two-dimensional block of material 600 with length l and width w.

If the hypothetical block of material 600 is a PPR material, when the block of material 600 is compressed along its width w, the material deforms into the shape shown as block 602. The width w1 of block 602 is less than the width w of block 600, and the length l1 of block 602 is greater than the length l of block 600: the material compresses along its width and expands along its length.

By contrast, if the hypothetical block of material 600 is an NPR material, when the block of material 600 is compressed along its width w, the material deforms into the shape shown as block 604. Both the width w2 and the length l2 of block 604 are less than the width w and length l, respectively, of block 600: the material compresses along both its width and its length.

NPR materials for integration into medical implants can be foams, such as polymeric foams, ceramic foams, metallic foams, or combinations thereof. A foam is a multi-phase composite material in which one phase is gaseous and the one or more other phases are solid (e.g, polymeric, ceramic, or metallic). Foams can be closed-cell foams, in which each gaseous cell is sealed by solid material; open-cell foams, in which the each cell communicates with the outside atmosphere; or mixed, in which some cells are closed and some cells are open.

An example of an NPR foam structure is a re-entrant structure, which is a foam in which the walls of the cells are concave, e.g., protruding inwards toward the interior of the cells. In a re-entrant foam, compression applied to opposing walls of a cell will cause the four other, inwardly directed walls of the cell to buckle inward further, causing the material in cross-section to compress, such that a compression occurs in all directions. Similarly, tension applied to opposing walls of a cell will cause the four other, inwardly directed walls of the cell to unfold, causing the material in cross-section to expand, such that expansion occurs in all directions. NPR foams can have a Poisson's ratio of between −1 and 0, e.g., between −0.8 and 0, e.g., −0.8, −0.7, −0.6, −0.5, −0.4, −0.3, −0.2, or −0.1. NPR foams can have an isotropic Poisson's ratio (e.g., Poisson's ratio is the same in all directions) or an anisotropic Poisson's ratio (e.g., Poisson's ratio when the foam is strained in one direction differs from Poisson's ratio when the foam is strained in a different direction).

An NPR foam can be polydisperse (e.g., the cells of the foam are not all of the same size) and disordered (e.g., the cells of the foam are randomly arranged, as opposed to being arranged in a regular lattice). An NPR foam can have a characteristic dimension (e.g., the size of a representative cell, such as the width of the cell from one wall to the opposing wall) ranging from 0.1 µm to about 3 mm, e.g., about 0.1 µm, about 0.5 µm, about 1 µm, about 10 µm, about 50 µm, about 100 µm, about 500 µm, about 1 mm, about 2 mm, or about 3 mm.

Examples of polymeric foams for integration into medical implants include thermoplastic polymer foams (e.g., polyester polyurethane or polyether polyurethane); viscoelastic elastomer foams; or thermosetting polymer foams such as silicone rubber. Examples of metallic foams include metallic foams based on steel (e.g., stainless steel), copper, aluminum, titanium (e.g., $Ti_6Al_4V$, TiNbZr, or unalloyed titanium), or other metals, or alloys thereof, or ceramics composed of a metal oxide (e.g., aluminum oxide, titanium oxide, or zirconium oxide).

In some implementations, austenitic stainless steels (e.g., 316L stainless steel) are particularly useful as NPR materials in medical implants. For example, some austenitic stainless steels have low carbon concentrations (e.g., about 0.1%) and are highly corrosion-resistant in body fluids. Austenitic stainless steels forming an NPR material may include nickel and chromium, in some implementations with concentrations 16% to 30% chromium and 2% to 20% nickel.

NPR-PPR composite materials are composites that include both regions of NPR material and regions of PPR material. NPR-PPR composite materials can be laminar composites, matrix composites (e.g., metal matrix composites, polymer matrix composites, or ceramic matrix composites), particulate reinforced composites, fiber reinforced composites, or other types of composite materials. In some examples, the NPR material is the matrix phase of the composite and the PPR material is the reinforcement phase, e.g., the particulate phase or fiber phase. In some examples, the PPR material is the matrix phase of the composite and the NPR material is the reinforcement phase.

Medical implants that include NPR materials can provide various benefits. First, because NPR materials are often less dense than counterpart PPR materials made of the same underlying compounds (e.g., NPR stainless steel may be less dense than PPR stainless steel), medical implants that include at least some NPR material can be lighter than PPR medical implants, reducing stress on bones, joints, muscles, and fixations.

Second, because NPR materials compress along a first axis in response to compression along a second axis orthogonal to the first axis, medical implants that include NPR materials can be less likely to expand over time and thereby overstress bones, joints, muscles, and fixations. For example, if bone growth or another bodily change over time compresses a PPR material, the PPR material may tend to expand in an orthogonal direction and apply pressure to tissue or bones in that orthogonal direction. By contrast, an NPR material subject to the same compression will tend to compress, not expand, in the orthogonal direction, without putting additional pressure on the tissue or bones, to maintain homeostasis.

Third, the use of NPR materials in or around implant fixations can improve the strength of healed bones and joints. This improvement is based on the dynamics of bone healing under a load. A bone plate that holds together sections of bone during healing performs a load-bearing function that the sections of bone would ordinarily perform when healed. However, with the bone plate performing that function, the sections of bone may not develop the strength necessary to bear the entire load. Rather, the sections of bone may instead develop only whatever strength is required of them, which, with the bone plate in place, is less than their ideal fully-healed strength. In practice, this means that bone mass can decrease over time as more and more load-bearing function is transferred to the bone plate. In some cases, the bone plate is left inside permanently, being necessary to support weakened, decayed bones.

In some cases, when NPR material is incorporated into a bone plate system (for example, in the bone plate, in a bone screw, or in a separate component disposed between the bone screw and bone, such as a sleeve, washer, or grommet, or in two or more of these components), as a load applied to the connected bone sections increases, the NPR material is correspondingly compressed by the load. Because of the negative Poisson's ratio of the NPR material, the NPR compresses in a transverse direction rather than displacing. This overall compression causes proportionally more of the load to be borne by the bone sections rather than by the bone plate, reducing or preventing loss of bone mass over time. And, because compression of the NPR material is caused by an increasing load, the system is at least partially self-regulating over a series of stable equilibria. A gradual increase in load over time, as bones heal, causes a corresponding gradual compression of the NPR material and, thereby, a corresponding transfer of load-bearing function to the bone rather than the bone plate.

Figure 7A:
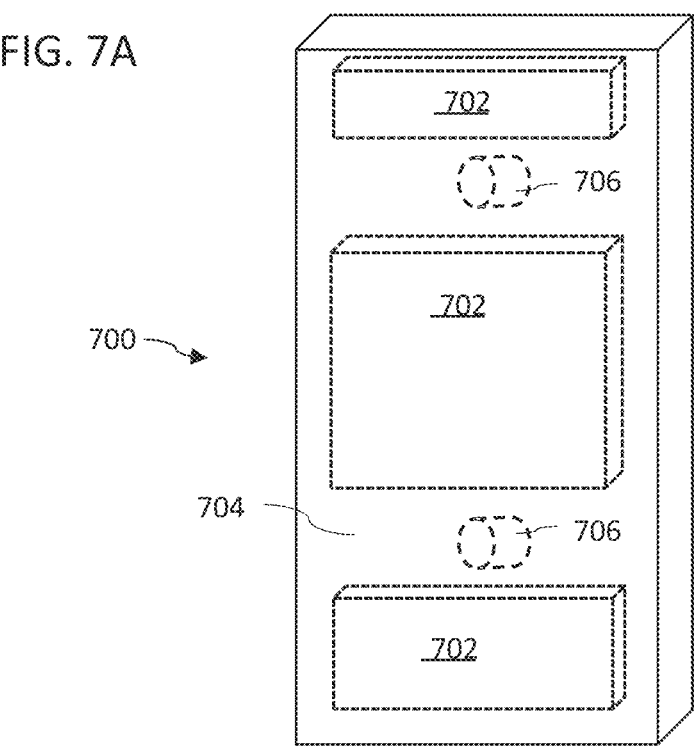

Integration of NPR materials into medical implants can take various forms. In some implementations, an NPR material is integrated into a body of a medical implant. For example, FIG. 7A shows a bone plate 700 having several NPR internal portions 702 embedded in a PPR portion 704. Screw holes 706 transect the bone plate 700, in this example through the PPR portion 704. In this example, the NPR internal portions 702 are entirely embedded in the PPR portion 704, such that outer surfaces of the bone plate 700 are composed of PPR material. However, in some implementations, at least some NPR material is not entirely embedded in PPR material but, rather, is exposed at a surface of the bone plate 700.

Figure 7B:
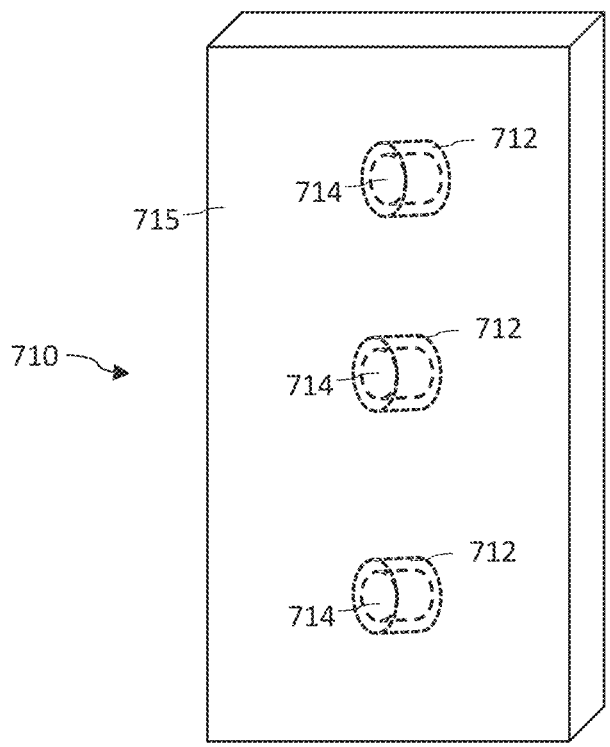

FIG. 7B shows an example of a bone plate 710 including NPR portions 712 embedded in a PPR portion 715. In this example, the NPR portions 712 are localized around screw holes 714. For example, the NPR portions 712 may include inner surfaces of the screw holes 714 (e.g., the inner surfaces that contact bone screws inserted through the screw holes 714). Because the NPR portions 712 behave as an intermediate linking section between, on one side, bone and bone screws, and, on another side, the rest of the bone plate 710, the NPR portions 712 can compress in response to increasing load and regulate relative loads borne by the bone plate 710 and bone sections held together by the bone plate 710.

FIGS. 7C-7E show perspective and cross-sectional diagrams of an example of a bone plate 720 that includes an internal, continuous NPR portion 722 enclosed within a PPR portion 724. Screw holes 726 transect the bone plate 720, passing through, from one side 728 of the bone plate 720 to an opposite side 730, PPR material, NPR material, and PPR material, in that order.

An overall width 732 of the bone plate 720 includes a width 734 of the NPR portion 724 and surrounding widths 736 of the PPR portion enclosing the NPR portion 724.

Absolute and relate thicknesses, widths, and lengths of NPR portions and PPR portions depend on, among other possible factors, a shape and size of the medical implant, choices of the NPR material and, if applicable, the PPR material, and a purpose of the medical implant. In some implementations, for a bone plate with the internal NPR portion 722, the width 734 of the NPR portion 722 may represent between 5% and 95% of the overall width 732, such as between 5% and 15%, between 15% and 25%, between 25% and 35%, between 35% and 45%, between 45% and 55%, between 65% and 75%, between 75% and 85%, or between 85% and 95%. For example, the NPR portion 724 may have a width 734 between 1 mm and 5 cm, such as between 1 mm and 5 mm, between 1 mm and 1 cm, between 5 mm and 1.5 cm, between 1 cm and 2 cm, between 2 cm and 3 cm, or between 3 cm and 5 cm.

As shown in FIG. 7E, an overall thickness 740 of the bone plate 720 includes a thickness 742 of the NPR portion 722 and surrounding thicknesses 744 of the PPR portion enclosing 724 the NPR portion. In some implementations, the thickness 742 of the NPR portion 722 may represent between 5% and 95% of the overall thickness 740, such as between 5% and 15%, between 15% and 25%, between 25% and 35%, between 35% and 45%, between 45% and 55%, between 65% and 75%, between 75% and 85%, or between 85% and 95%. For example, the NPR portion 724 may have a thickness 742 between 0.5 mm and 2 cm, such as between 0.5 mm and 1 mm, between 0.5 mm and 2 mm, between 0.5 mm and 5 mm, between 0.5 mm and 1 cm, between 5 mm and 1.5 cm, or between 1 cm and 2 cm.

In some implementations, a PPR material enclosing an NPR material has characteristics suitable for contact with tissue. For example, the PPR material may be non-toxic and corrosion-resistant. This can allow for the use of internal NPR materials that may not meet these standards. However, some NPR materials (e.g., NPR stainless steel) are themselves non-toxic and corrosion-resistant and therefore suitable direct tissue contact.

In some implementations, all or substantially all of a bone plate may be formed of an NPR material. In some implementations, a bone plate may include an outer portion of NPR material enclosing an inner PPR portion.

Figure 7F:
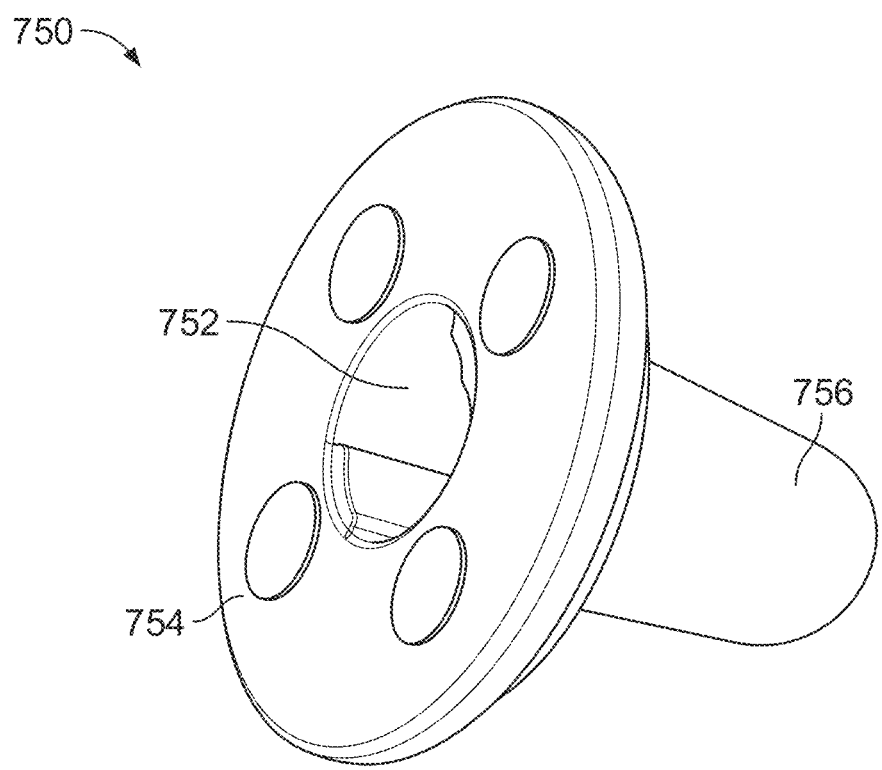
FIG. 7F is a diagram of an example grommet.
Figure 7G:
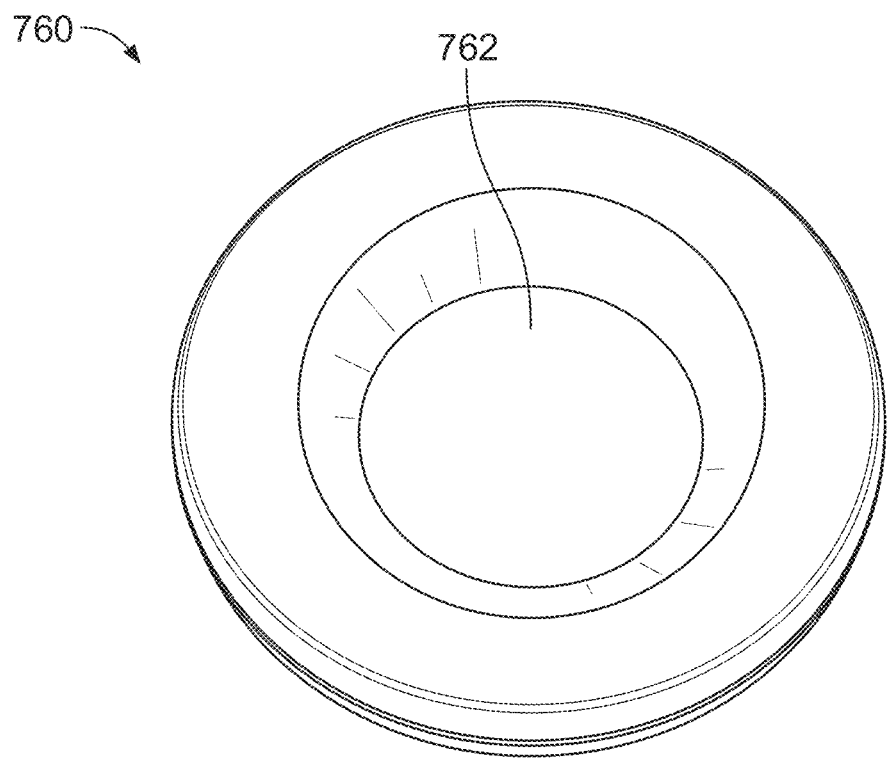
FIG. 7G is a diagram of an example washer.

In some implementations, NPR material is included in an intermediate component disposed between a bone screw and bone, such as a sleeve, washer, or grommet. For example, as shown in FIGS. 7F-7G, a grommet 750 and/or washer 760 may include NPR material, such as stainless steel, or a titanium-containing metal such as $Ti_6Al_4V$. The NPR material can make up the entire grommet 750 and/or washer 760, an inner or outer portion of the grommet 750 and/or washer 760, or another section of the grommet 750 and/or washer 760, as described for medical implants in various implementations throughout this disclosure. In some implementations, the grommet 750 and/or washer 760 is coated with one or more ceramics, e.g., carbon or hydroxyapatite.

The grommet 750 includes a washer portion 754 and a protruding portion 756, either or both of which can include the NPR material.

A bone screw can be inserted through the aperture 752 of the grommet 750 and/or the aperture 762 of the washer 760 to secure a bone plate to bone. As the bone heals and load on the grommet 750 and/or washer 760 increases, the NPR material of the grommet 750 and/or washer 760 compresses without expanding in a transverse direction, regulating load transfer to the bone plate and causing the bone to heal with greater strength.

The grommet 750 and washer 760 can have dimensions suitable to their intended use. For example, the apertures 752, 762 may have diameters between 1.5 mm and 6.5 mm, such as between 1.5 mm and 4.5 mm or between 3.5 mm and 6.5 mm.

NPR portions of medical implants such as the bone plates shown in FIGS. 7A-7E, the grommet shown in FIG. 7F, and the washer shown in FIG. 7G, can be produced in a variety of ways. In some implementations, an initially PPR material (sometimes referred to as a "precursor material") is converted into the NPR material. For example, a porous PPR sponge or foam can be transformed to change its structure into a structure that exhibits a negative Poisson's ratio. In some examples, NPR foams are produced by transformation of nanostructured or microstructured PPR materials, such as nanospheres, microspheres, nanotubes, microtubes, or other nano- or micro-structured materials, into a foam structure that exhibits a negative Poisson's ratio. The transformation of a PPR foam or a nanostructured or microstructured material into an NPR foam can involve thermal treatment (e.g., heating, cooling, or both), application of pressure, or a combination thereof. In some examples, PPR materials, such as PPR foams or nanostructured or microstructured PPR materials, are transformed into NPR materials by chemical processes, e.g., by using glue. In some examples, NPR materials are fabricated using micromachining or lithographic techniques, e.g., by laser micromachining or lithographic patterning of thin layes of material. In some examples, NPR materials are fabricated by additive manufacturing (e.g., three-dimensional (3D) printing) techniques, such as stereolithography, selective laser sintering, or other appropriate additive manufacturing technique.

In an example, a PPR thermoplastic foam, such as an elastomeric silicone film, can be transformed into an NPR foam by compressing the PPR foam, heating the compressed foam to a temperature above its softening point, and cooling the compressed foam. In an example, a PPR foam composed of a ductile metal can be transformed into an NPR foam by uniaxially compressing the PPR foam until the foam yields, followed by uniaxially compression in other directions.

Figure 8:
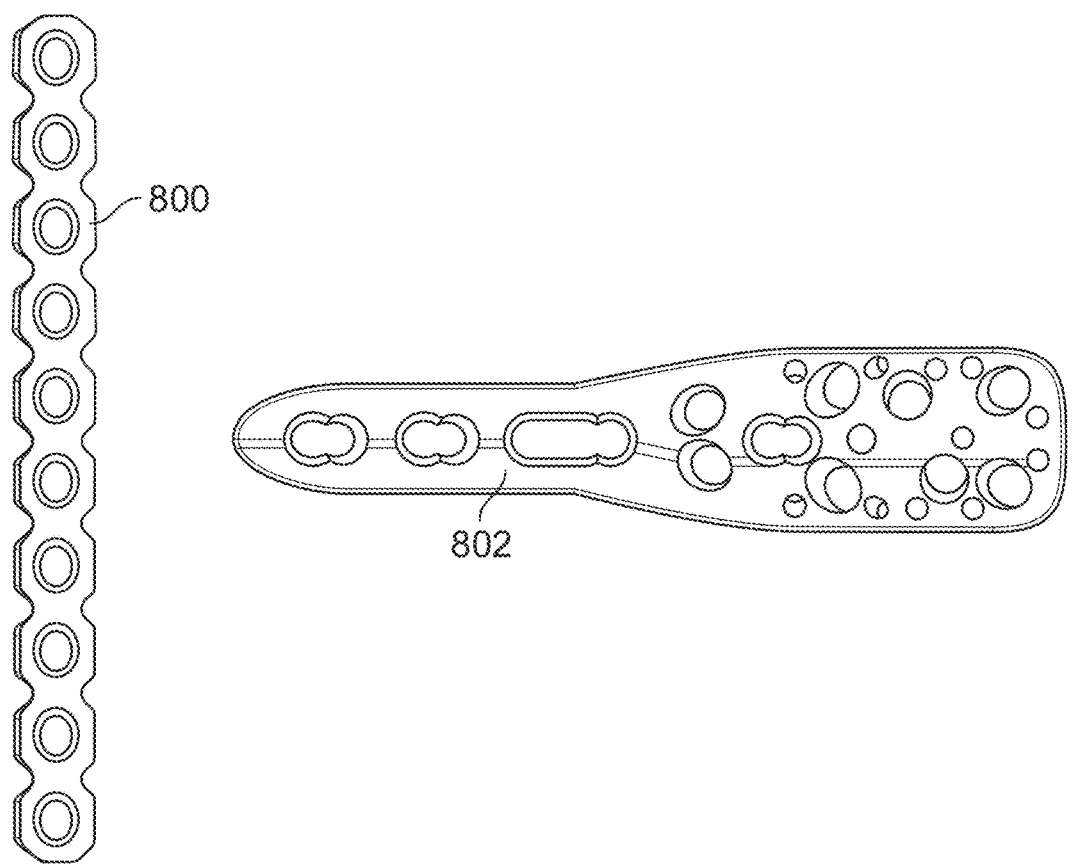
FIG. 8 is a diagram of several example bone plates.
Figure 8:
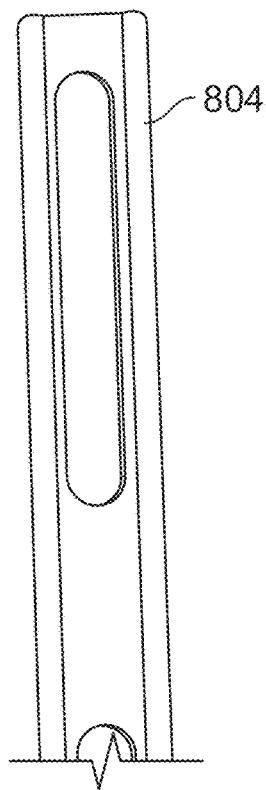

Bone plates including an NPR material may have various shapes, sizes, and configurations based on their intended surgical purpose. FIG. 8 illustrates three possible shapes 800, 802, 804 and configurations among the many possibilities. Screw holes can be configured to receive locking screws, non-locking screws, or either type of screw. In some implementations, bone plates are contoured, e.g., to accommodate a bone flare near the metaphysis.

Bone screws represent another important aspect of implant fixation and, like bone plates, can be formed at least partially of NPR material. The inclusion of NPR material can lighten the bone screws, reduce or eliminate compression-induced expansion of the bone screws, and regulate relative loads borne by bone plates and healing bones.

Figure 9:
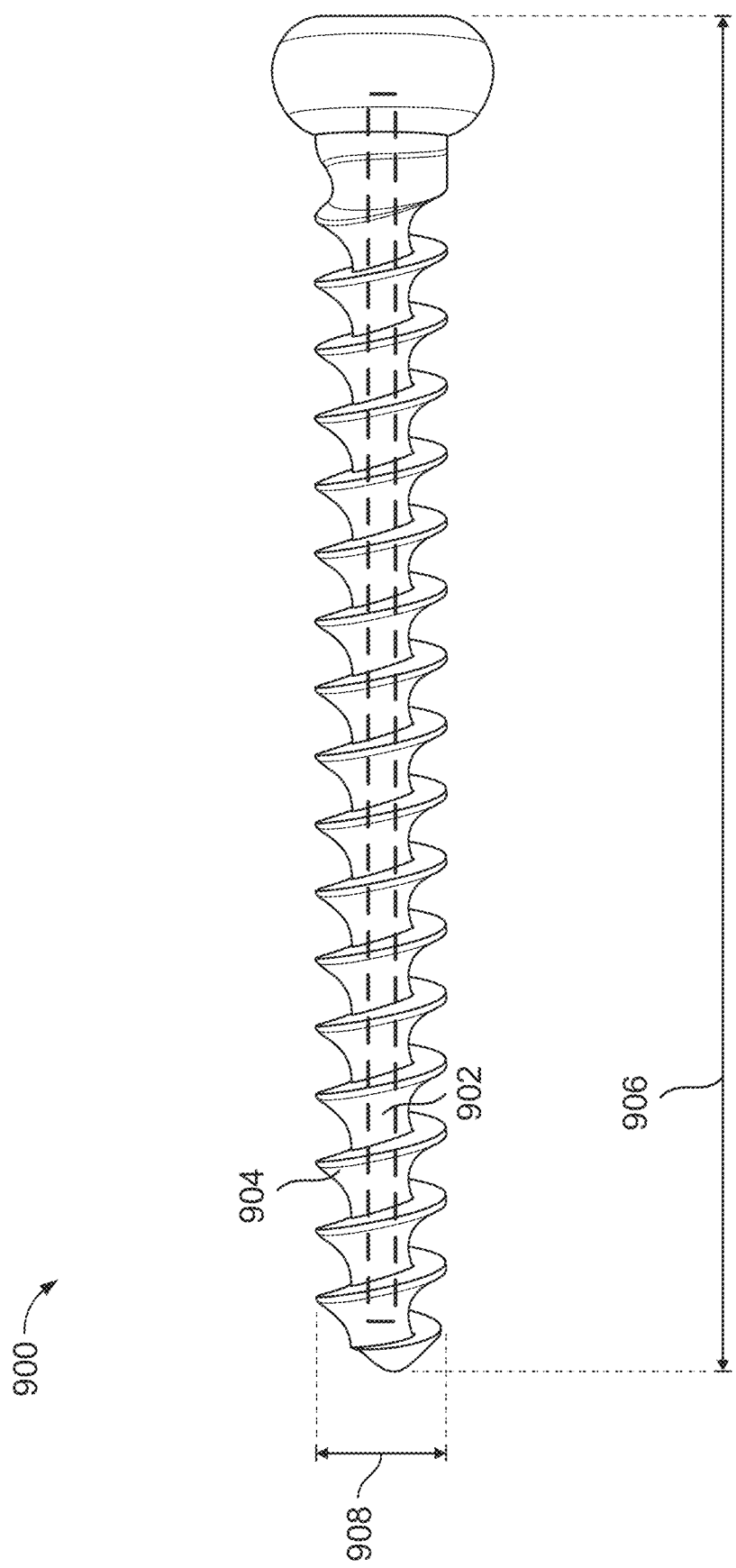
FIG. 9 is a diagram of an example bone screw.
Figure 10A:
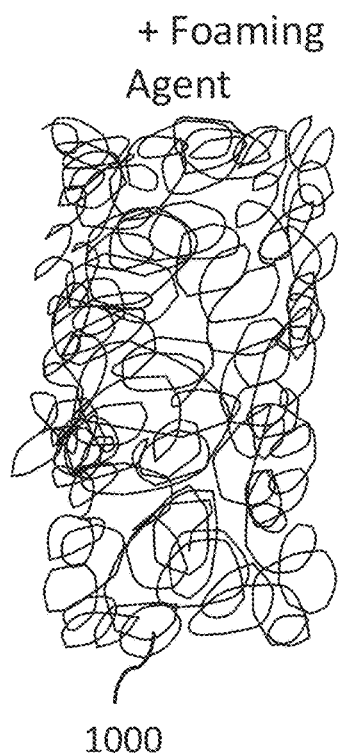
FIGS. 10A-10E are diagrams showing an example method of making a medical implant.
Figure 10B:
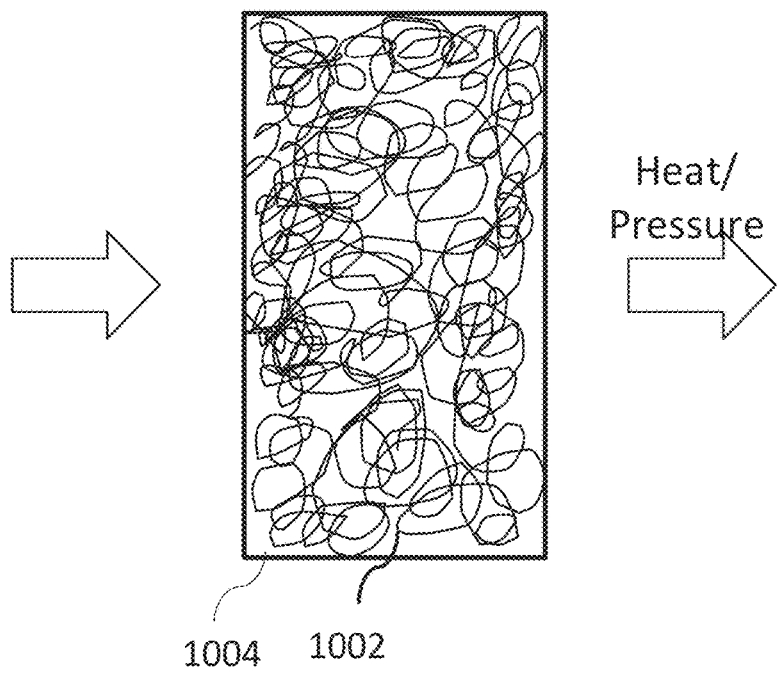
Figure 10C:
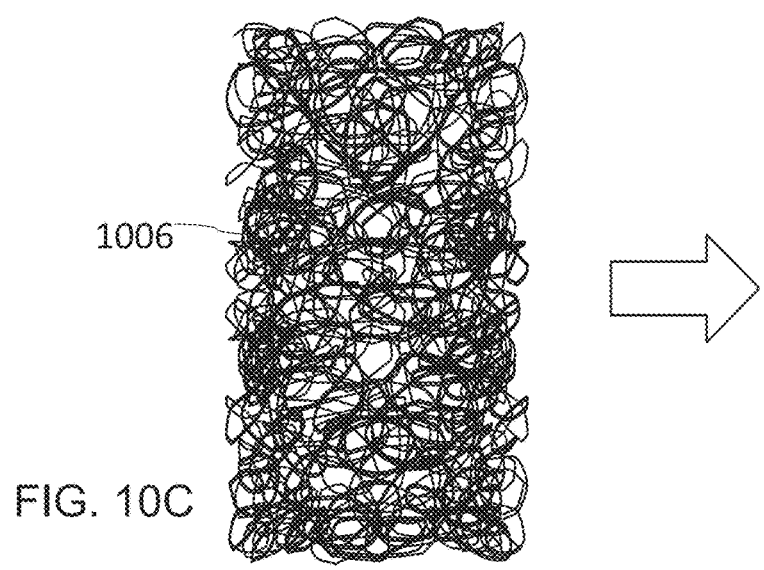
Figure 10D:
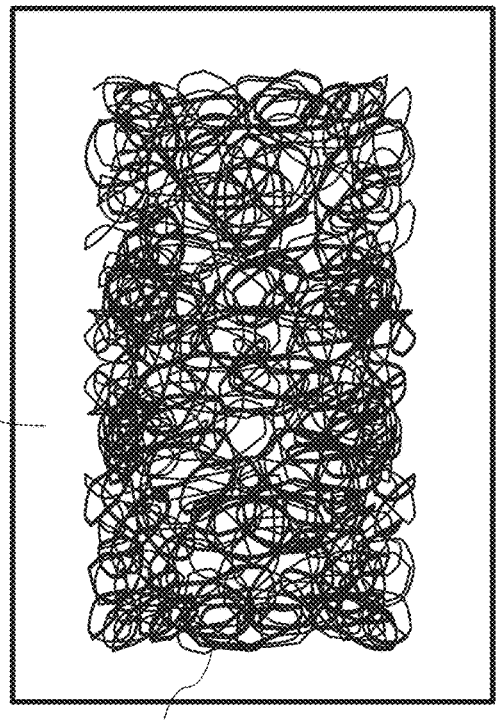
Figure 10E:
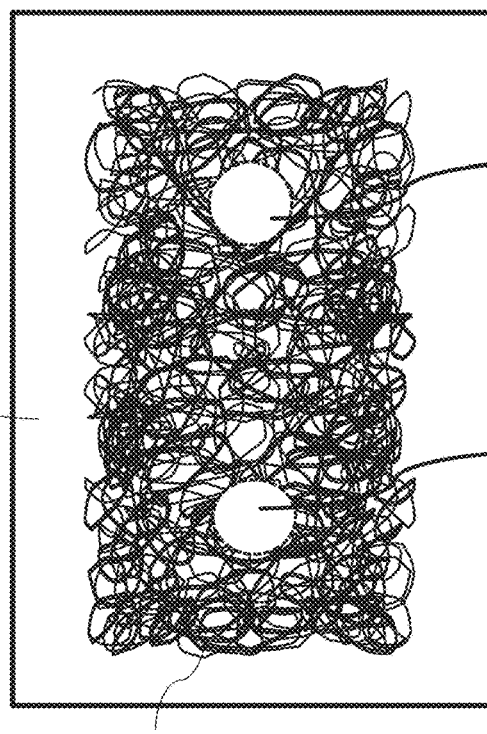

FIG. 9 shows an example bone screw 900 including an internal NPR portion 902 embedded in a PPR portion 904, which may be composed of PPR stainless steel, titanium, or another material. Depending on its intended use, the bone screw 900 can have a length 906 between 5 mm and 120 mm, or another length, and a diameter 908, including treads, between 1.5 mm and 6.5 mm, or another diameter. In some implementations, the bone screw 900 is a cortical bone screw and has a diameter 908 between 1.5 mm and 4.5 mm. In some implementations, the bone screw 900 is a cancellous bone screw having a diameter 908 between 3.5 mm and 6.5 mm.

FIGS. 10A-10E illustrate an example method of making a medical implant, such as a bone plate, having an internal NPR portion. A granular or powdered material 1000, such as a polymer material (e.g., a rubber) or a metal (e.g., stainless steel) is mixed with a foaming agent to form a porous material (e.g., a sponge or a foam) 1002. The porous material 1002 is placed into a mold 1004. Pressure is applied to compress the porous material 1002, and the compressed porous material 1002 is heated to a temperature above its softening point. The compressed, heated porous material 1002 is then allowed to cool, resulting in an NPR material 1006. The NPR material 1006 is covered with an outer PPR material 1008, which is adhered to the NPR material 1006. In some implementations, heat and pressure applied again to cure and/or bond together the NPR material 1006 and the PPR material 1008 to form a cohesive structure. In the case of a bone plate, screw holes 1010 can be formed (e.g., tapped) in the resulting structure.

The PPR material, whether in a bone plate or in other medical implants described in this disclosure, may be a metal (e.g., stainless steel, titanium or aluminum), a polymer such as ultra-high-molecular-weight polyethylene (UHMWPE) or another plastic, or another type of material, or combinations thereof.

Figures 11A, 11B:
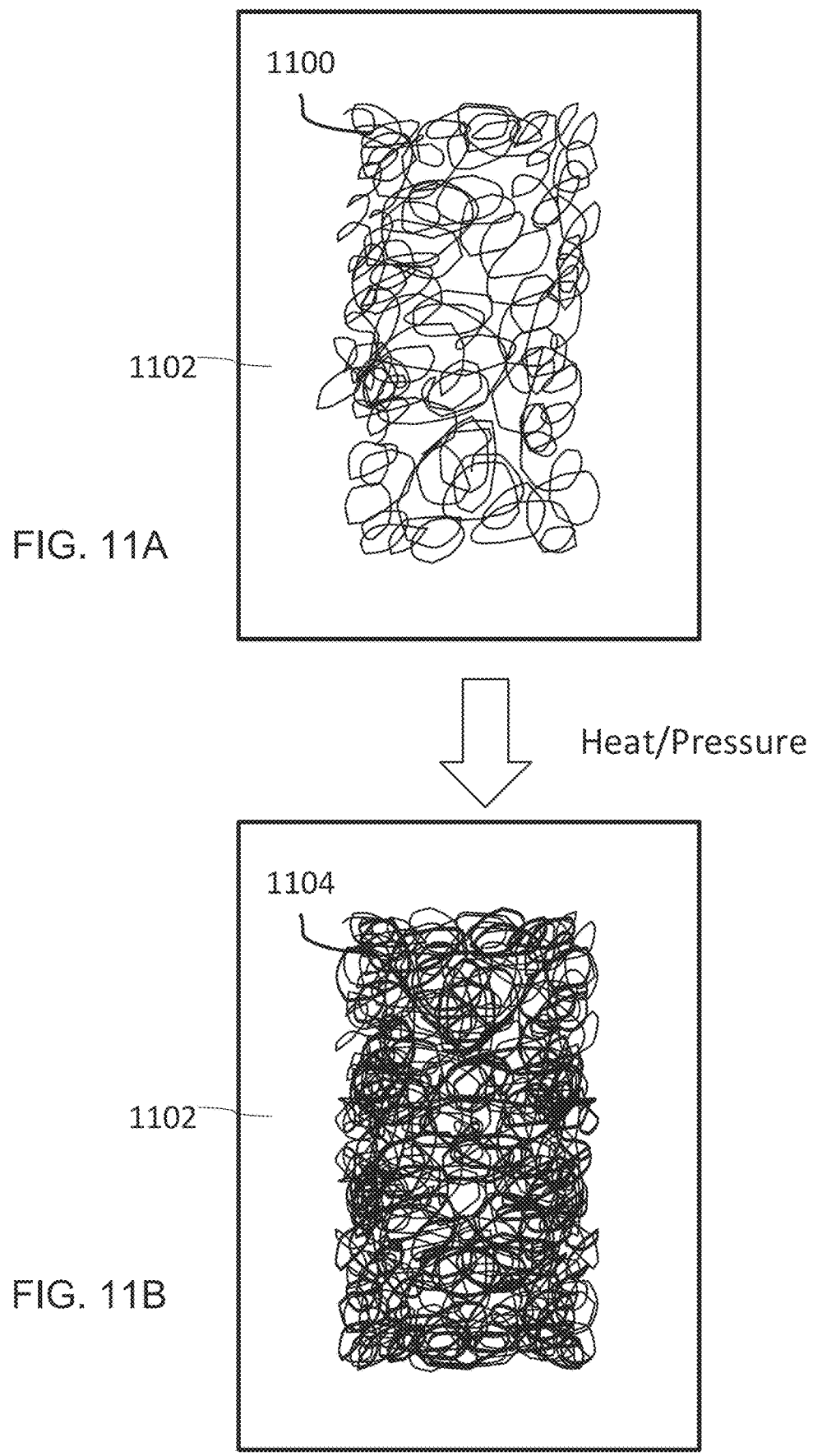
FIGS. 11A-11B are diagrams showing an example method of making a medical implant.

FIGS. 11A-11B show an example of a method of fabricating a medical implant with an internal NPR portion. As shown in FIG. 11A, a precursor material 1100 is enclosed in a PPR material 1102. In some implementations, the precursor material 1100 and the PPR material 1102 are adhered and/or bonded together.

Heat and/or pressure are applied to convert the precursor material 1100 into an NPR portion 1104 enclosed in the PPR material 1102. In some implementations, the heat and/or pressure that convert the precursor material 1100 into the NPR portion 1104 concurrently cure and/or bond together the NPR portion 1104 and the PPR material 1102, reducing fabrication complexity and cost.

Other methods can also be used to fabricate a medical implant including an NPR material or an NPR-PPR composite material, such as a bone plate or a prosthetic. For example, various additive manufacturing (e.g., 3D printing) techniques, such as stereolithography, selective laser sintering, or other appropriate additive manufacturing technique, can be implemented to fabricate a medical implant including an NPR material or an NPR-PPR composite. In some examples, different components of the medical implant are made by different techniques. For example, an internal NPR portion may be 3D printed while the outer PPR portion is not, or vice versa. In some implementations, some or all of a medical implant that includes NPR material can be found in a lost-wax casting process.

NPR material included in medical implants, according to implementations of this disclosure, need not be entirely contained within a PPR material. For example, in some medical implants described above, NPR material is exposed at least inside screw holes through which bone screws can be inserted. In various implementations, NPR material included in a medical implant may be entirely embedded in a PPR material, partially embedded in a PPR material and partially exposed, or entirely exposed, e.g., for a medical implant or a component of a medical implant entirely made of an NPR material (also within the scope of this disclosure), or, as described in more detail below, for a medical implant or a component of a medical implant in which an NPR material forms an outer layer.

Having an NPR material form an outer layer of a medical implant can provide advantages in some implementations. The tendency of the NPR material to compress in a transverse direction, rather than expand, in response to compression can reduce stress or strain that may be applied to components or body parts in contact with the medical implant, or otherwise help to maintain homeostasis. The outer NPR material may compress in response to outward-directed force from the internal PPR material, and/or may expand in response to an inward-directed force (a pulling force) from the internal PPR material, maintaining a more constant total volume of the medical implant over time. And the NPR material may be lighter than a comparable PPR material.

Figure 12:
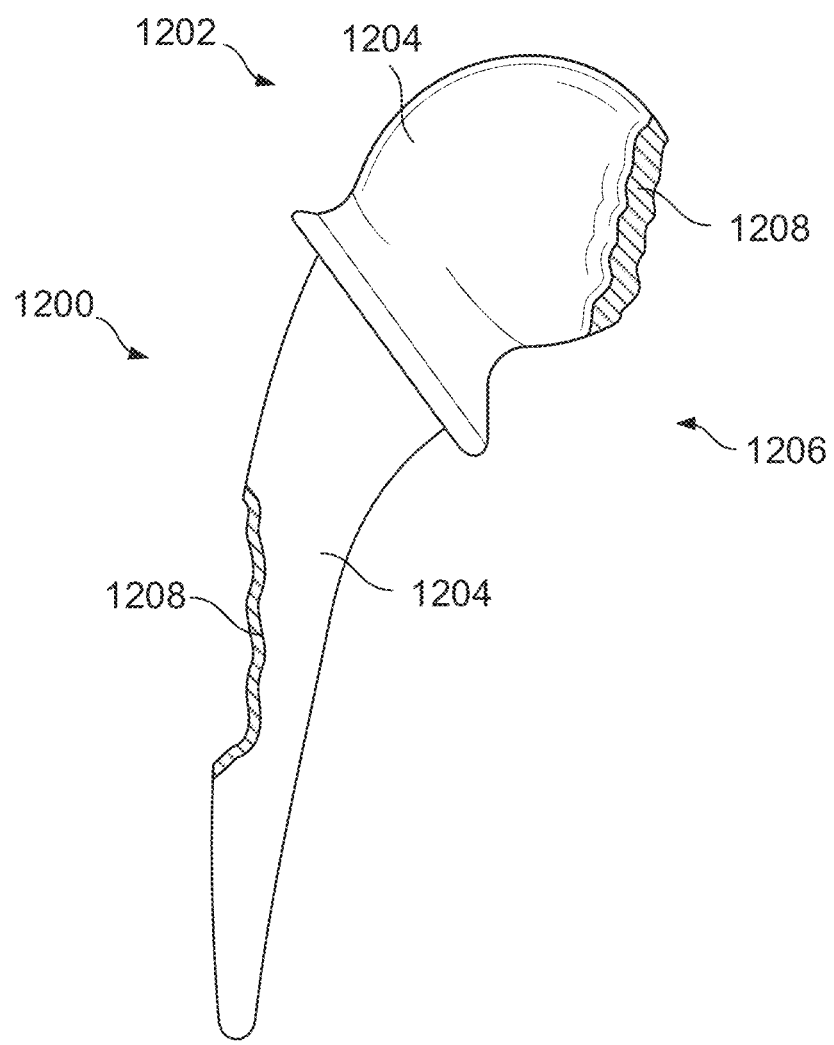
FIG. 12 is a diagram showing an example prosthetic hip.
Figure 13A:
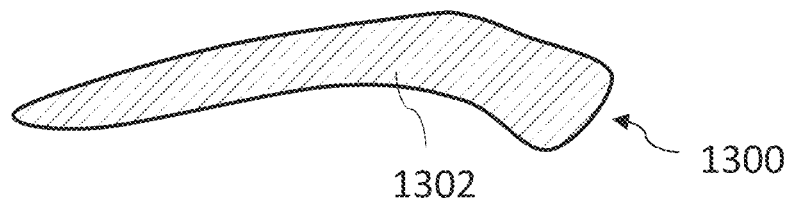
FIGS. 13A-13D are diagrams showing an example method of making a medical implant.
Figure 13B:
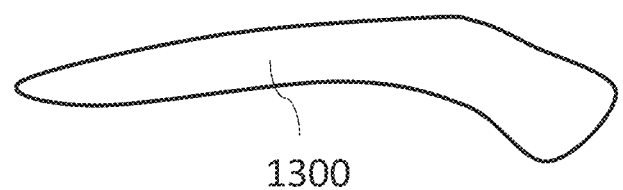
Figure 13C:
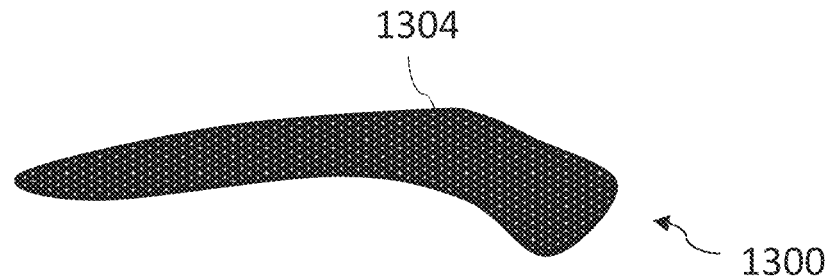
Figure 13D:
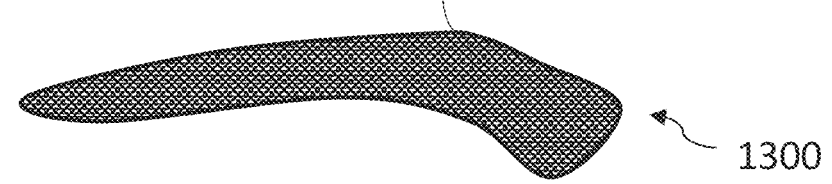

FIG. 12 shows a stem 1200 and ball 1202 of an example hip prosthesis 1206. As described above, the stem 1200 is configured to be fixed to a femur, while the ball 1202 is configured to rotate within a cup, which may be prosthetic or natural. The ball 1202 may be fixed to the stem 1200 by screws, by adhesive, or by another fixation method.

In this example, the stem 1200 and ball 1202 each include an outer NPR layer 1204 over an internal PPR portion 1208. For example, the outer NPR layer 1204 may be a pre-coating layer. A pre-coating layer can be arranged between a primary material that forms the main body of a medical implant (for example, a metal or a polymer) and bone cement that bonds the medical implant to bone. The pre-coating layer improves the fixation of the medical implant to the bone, compared to a fixation based on adhering the primary material directly to the bone cement. For example, the NPR material may include a polymer and/or a material that is also used as a bone cement, such as polymethyl methacrylate or a polymethylmethacrylate-methylmethacrylate-styrene copolymer. In some implementations, the NPR material is substantially completely polymerized and is chemically bondable with the bone cement.

Instead of, or in addition to, serving a fixation-improvement function, the outer NPR layer 1204 may promote bone ingrowth to speed up the process of bone fixation. Example of materials usable in an NPR form for this purpose are hydroxyapatite ($Ca_{10}(PO)_4OH_2$), growth factors, bone morphogenic proteins, and mixtures thereof. The material(s) that form the outer NPR layer 1204 (e.g., polymethyl methacrylate or hydroxyapatite) can be first provided in PPR form (e.g., as a porous foam) and then converted to NPR form by heat and/or pressure.

In some implementations, the NPR layer 1204 has a thickness between 0.1 mm and 5 mm, such as between 0.5 mm and 3 mm, between 1 mm and 5 mm, between 1 mm and 3 mm, or about 2 mm.

The stem 1200 and ball 1202 need not both include an outer NPR coating. Rather, in some implementations only the stem 1200 or only the ball 1202 includes the NPR coating. Moreover, some hip prostheses include the ball 1202 and not the stem 1200 (e.g., the ball 1202 attached to a natural femur), or include the stem 1200 and not the ball 1202 (e.g., an artificial femur prosthetic attached to a natural head); these implementations are also within the scope of this disclosure.

Moreover, in some implementations, instead of or in addition to including an outer NPR coating, a prosthesis may include an embedded NPR portion as described in reference to FIGS. 7A-7E, which may reduce the weight of the prosthesis and improve stress/strain characteristics of the prosthesis compared to entirely PPR prostheses.

FIGS. 13A-13D illustrate an example method of making a medical implant, such as a prosthetic hip component, having an outer NPR material layer. An initial component 1300 is formed of one or more of PPR material(s), one or more NPR-PPR composite materials, and/or one or more NPR material(s). For example, the initial component 1300 may include an internal NPR portion to reduce a weight of the initial component 1300, the internal NPR portion embedded in a PPR portion.

In some implementations, the initial component 1300 has an outer oxide layer 1302, e.g., a native titanium oxide layer. This outer oxide layer 1302 may optionally be removed prior to coating of the initial component 1300 in a precursor material. For example, the outer oxide layer 1302 may be removed by a chemical treatment such as an acid treatment, physical abrasion, or a combination thereof. Removal of the oxide layer 1302 may improve adhesion between the initial component 1300 and additional layers such as pre-coating layers and bone cement layers.

With or without removal of the possible outer oxide layer 1302, a coating of precursor material 1304 (e.g., a porous or spongy ceramic, metal, polymer, and/or composite, as described throughout this disclosure) is provided on the outer surface of the initial component 1300. Pressure and/or heat are applied to convert the precursor material 1304 into an NPR coating 1306. For example, the initial component 1300 with the coating of precursor material 1304 may be placed into a mold, pressure applied by the mold to compress the precursor material 1304, and heat applied to the compressed precursor material 1304 to heat the compressed precursor material 1304 to a temperature above its softening point. The compressed, heated precursor material 1304 is then allowed to cool, resulting in a prosthetic component with an outer NPR coating 1306, e.g., the example femoral stem 1200.

In some implementations, the thickness and/or gradation of porosity of the coating of precursor material 1304 (and therefore of the NPR coating 1306) are controlled. To control the thickness, in some implementations the mold has precisely configured dimensions that impose a desired thickness on the coating of precursor material 1304, given known dimensions of the initial component 1300. To control the gradation of porosity, the pressure and/or heat used to form the NPR coating 1306 can be regulated. For example, one or more of a temperature at which the precursor material 1304 is heated, at rate of change of the temperature at which the precursor material 1304 is heated, a pressure applied to the precursor material 1304, or a rate of change of the pressure applied to the precursor material 1304 can be controlled to achieve a desired porosity. The porosity may be controlled such that an exposed surface of the NPR coating 1306 is substantially free of pores, which in some implementations improves adhesion to bone cement.

At time of insertion into a patient, a medical implant having an NPR outer coating (e.g., an NPR pre-coating to improve adhesion) is adhered to a bone of the patient by a bone cement such as polymethyl methacrylate (PMMA). Once the medical implant is adhered in place, the NPR outer coating can not only improve adhesion but can also help to maintain homeostasis and balance relative loads borne by the patient's bones and the medical implant.

Various types of medical implants, including bone plates, bone screws, hip prosthesis components, dental implant components, finger prosthesis components, tibia prosthesis components, artificial knee components, and spinal fusion components, can be configured as described in reference to FIGS. 7A-13D, e.g., can include an outer NPR coating, can include embedded NPR portion(s), can be entirely formed of NPR material, or can otherwise incorporate NPR material, to realize some or all of the NPR-linked advantages described in this disclosure.

Figure 14:
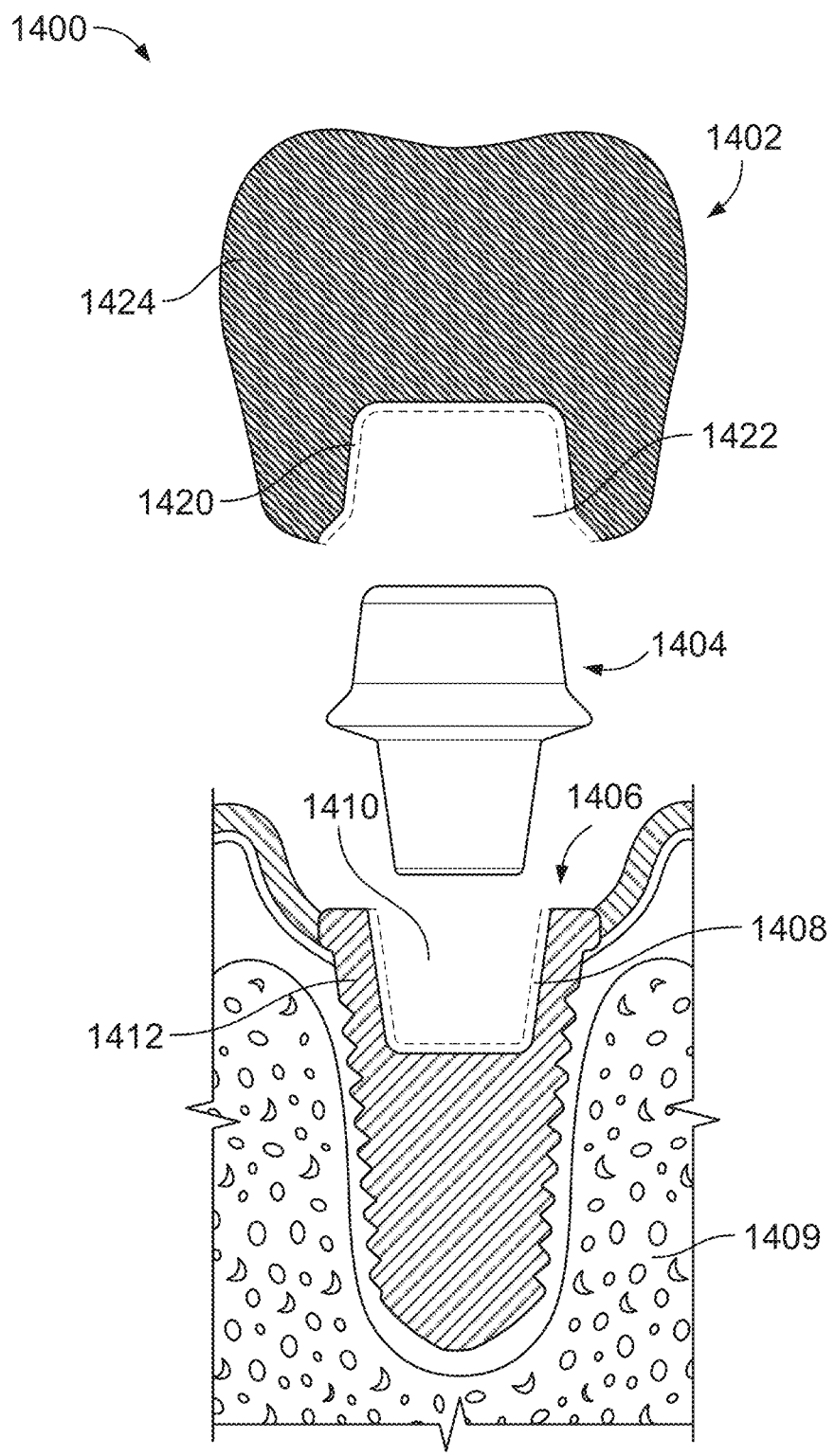
FIG. 14 is a cross-sectional view of an example dental implant.

FIG. 14 shows a cross-sectional view of an example of a medical implant incorporating NPR material. In this example, a dental implant 1400 includes a prosthetic tooth 1402, an abutment 1404, and a fixture 1406. At least one of the abutment 1404, the fixture 1406, and the prosthetic tooth 1402 include NPR material.

NPR material in the abutment 1404, if present, may maintain homeostasis between the prosthetic tooth 1402 and the fixture 1406 by compressing or expanding in response to stresses, balancing relative loads and stresses across the dental implant 1400. The abutment 1404 may be formed entirely of an NPR material, or the NPR material may form an inner and/or outer portion of the abutment 1404.

NPR material in the fixture 1406, if present, may be incorporated as shown in FIG. 14. The fixture 1406 includes an NPR portion 1408 in which a cavity 1410 is configured to receive the abutment 1404, and also includes a PPR portion 1412. The NPR portion 1408 acts as an intermediate layer between the abutment 1404 and the outer PPR portion 1412 of the fixture 1406, compensating for possible changes in volume or forces applied by the abutment 1404 and the PPR portion 1412 (e.g., by bone 1409).

NPR material in the prosthetic tooth 1402, if present, may be incorporated as shown in FIG. 14. The prosthetic tooth 1402 includes an NPR portion 1420 in which a cavity 1422 is configured to receive the abutment 1404, and also includes a PPR portion 1424. The NPR portion 1420 acts as an intermediate layer between the abutment 1404 and the PPR portion 1424 of the prosthetic tooth 1402, compensating for possible changes in volume or forces applied by the abutment 1404 and the PPR portion 1424.

Figure 15:
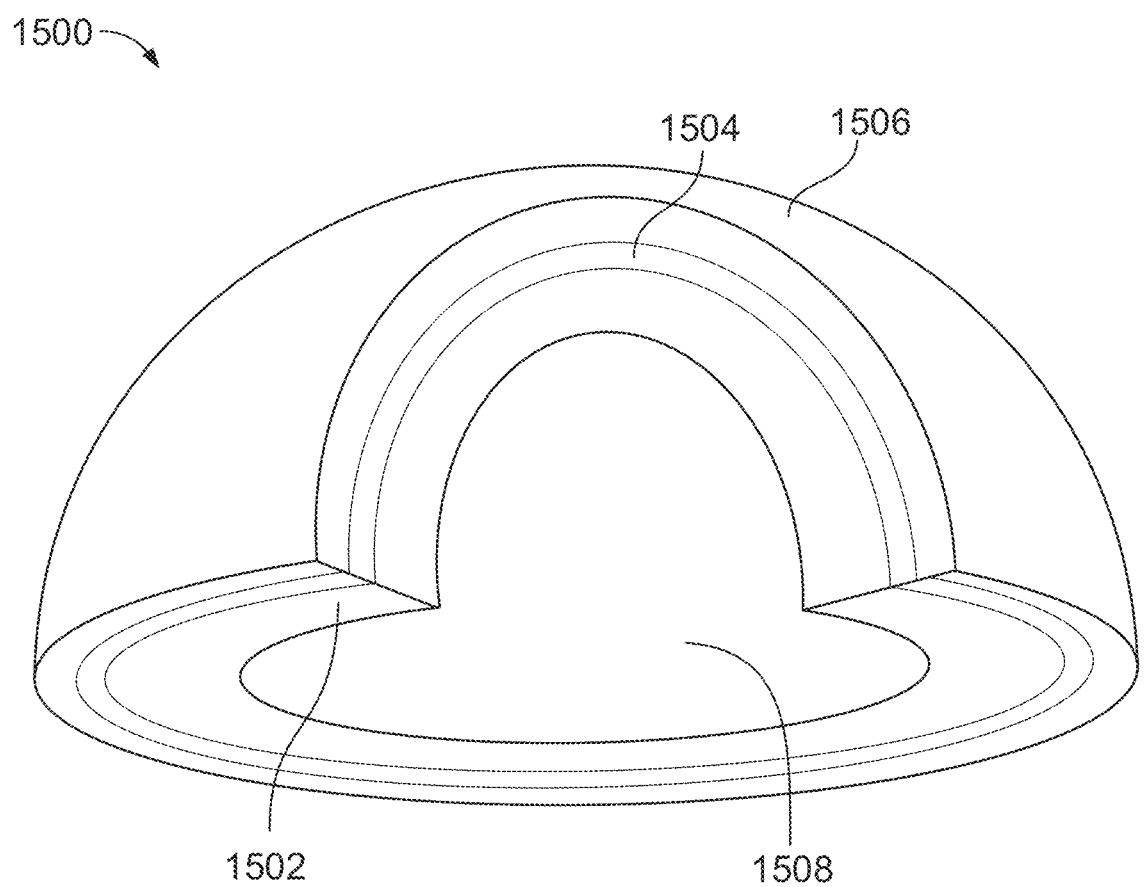
FIG. 15 is a cut-away cross-sectional view of an example acetabular cup.

FIG. 15 shows an example of an acetabular cup 1500 that includes NPR material. The acetabular cup 1500 partially encloses a hollow 1508 configured to receive a natural or prosthetic femoral head. In contact with the femoral head is an inner cup 1502, which may be formed of a polymer such as UHMWPE. An NPR coating 1504 coats the inner cup 1502, and a cement layer 1506 (which may in practice be applied at a time of installation of the acetabular cup into the pelvis) coats the NPR coating 1504, to fix the acetabular cup 1500 inside the pelvis.

As described above in the context of prosthetic femoral stems, the NPR coating 1504 can improve the adhesion between the inner cup 1502 and the cement layer 1506 (and therefore between the acetabular cup 1500 as a whole and the pelvis in which the acetabular cup 1500 is implanted). The NPR coating 1504 can also promote improved homeostasis in the acetabular cup-pelvis system by equilibrating stresses and compressing or expanding in response to changing pressures over time so as to maintain homeostasis. The NPR coating 1504 can have any or all of the characteristics disclosed for the NPR coating 1306 described in reference to FIG. 13D.

Figure 16:
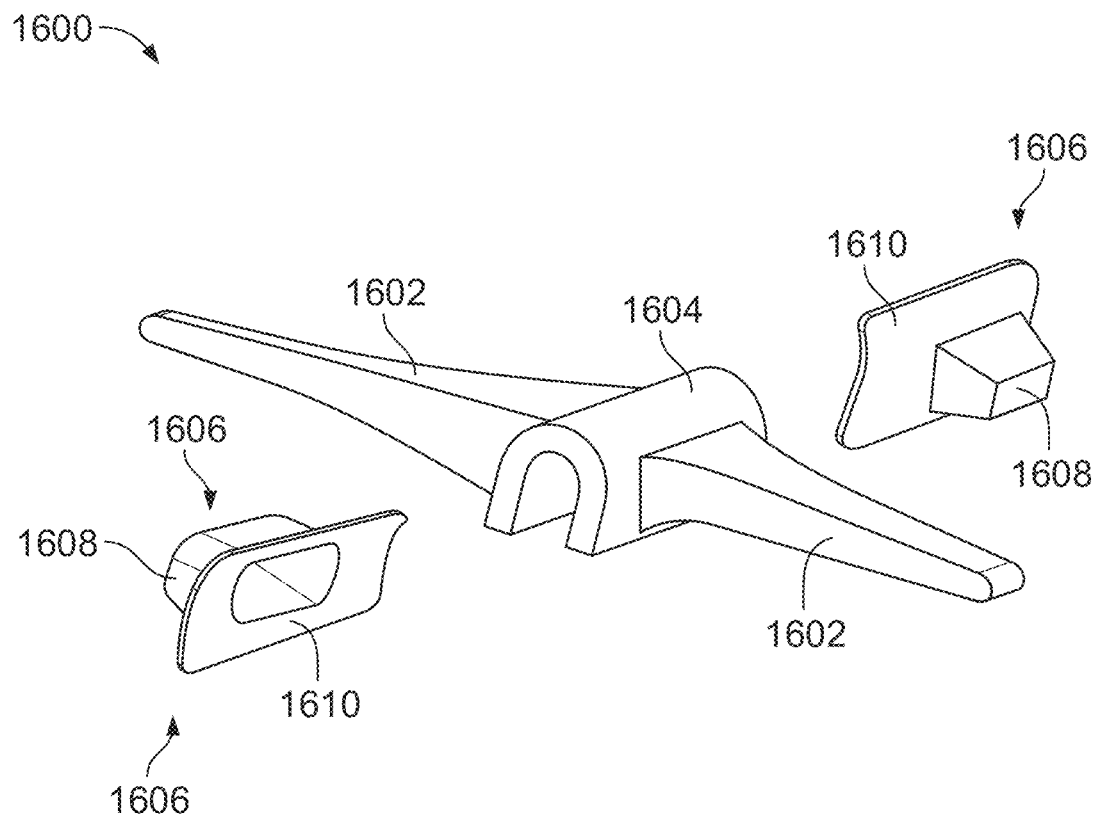
FIG. 16 is a diagram of an example prosthetic finger joint.

FIG. 16 shows an example of a finger joint prosthesis 1600 that includes NPR material. The finger joint prosthesis 1600 includes two stems 1602 that are affixed inside respective finger bones and joined by a hinge 1604 that allows movement of the two stems 1602 with respect to one another. Two grommets 1606 are placed between the stems 1602 and the respective finger bones in which the stems 1602 are inserted, acting as buffers between the stems 1602 and the finger bones. In this example, each grommet 1606 includes a protruding portion 1608 oriented away from the hinge 1604 when the prosthesis 1600 is in position on a finger, and a washer portion 1610 arranged between the hinge 1604 and surrounding tissue or bone.

The grommets 1606 reduce the likelihood that the stems 1602 and hinge 1604 (either or both of which may be composed of a tear-prone material such as silicone rubber) will tear due to pressure applied by the bones against the stems 1602 and hinge 1604. This pressure is instead applied to the interceding grommets 1606, which, if made of a PPR material, may expand in a transverse direction, potentially causing damage to the prosthesis 1600 and/or the finger in which the prosthesis 1600 is embedded.

To reduce or elimination expansion of the grommets 1604, and to reduce the weight of the prosthesis 1600, in some implementations the grommets 1606 are partially or entirely formed of an NPR material, e.g., an NPR metal such as stainless steel or a titanium-containing metal. In some implementations, the grommets 1606 include $Ti_6Al_4V$. The NPR portion(s) of the grommets 1606 can be formed as described throughout this disclosure, e.g., by application of heat and pressure to a porous precursor material.

In some implementations, the NPR grommets 1606 are coated with one or more ceramics, e.g., carbon or hydroxyapatite. A ceramic coating, such as a carbon or hydroxyapatite coating, can be included on any of the NPR-containing medical implants described in this disclosure.

Figure 17A:
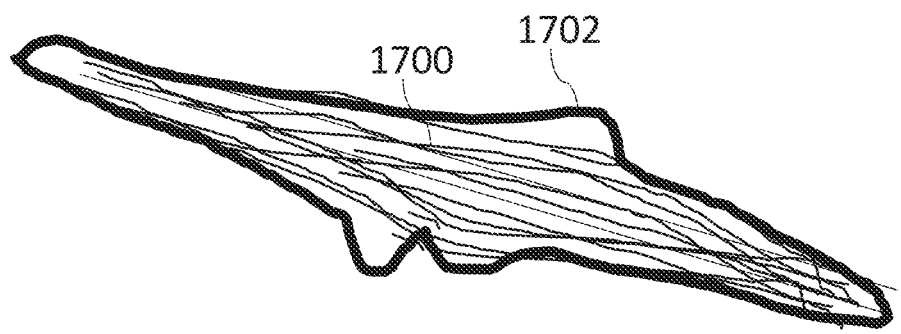
FIGS. 17A-17C are diagrams showing an example method of making a medical implant.
Figure 17B:
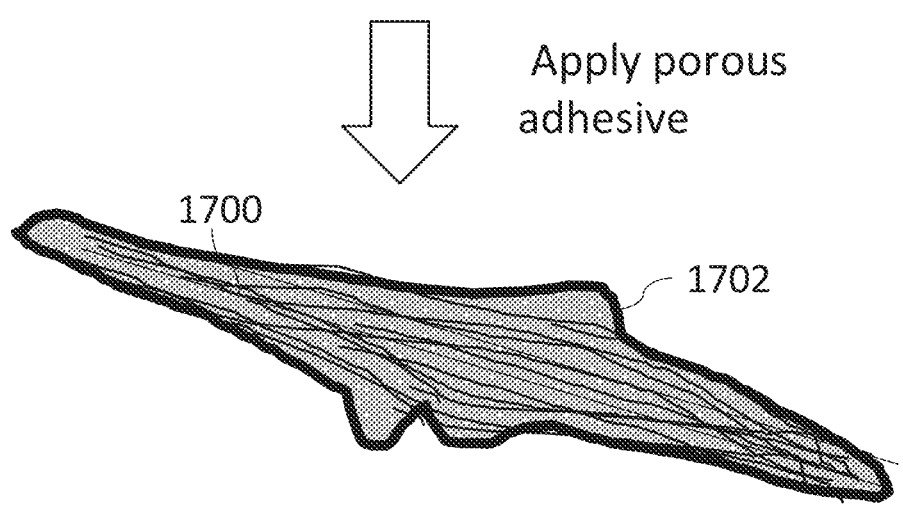
Figure 17C:
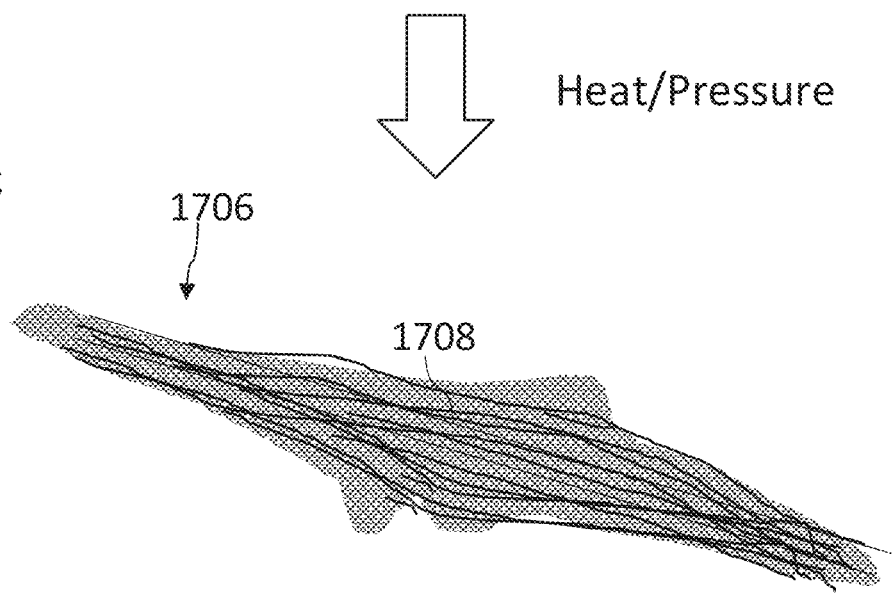

The stems 1602 and/or hinge 1604, instead of or in addition to the grommets 1664, may incorporate an NPR material. In some implementations, the stems 1602 are composed of polymer fibers embedded in an NPR binder. For example, to make NPR material including prostheses such as the example prosthesis 1600, as shown in FIGS. 17A-17C, biocompatible polymer fibers 1700 are placed in a mold 1702. The biocompatible polymer fibers 1700 may include one or more of polyethylene, polypropylene, Polytetrafluoroethylene (PTFE), a nylon, or another biocompatible fiber.

A porous adhesive such as adhesive silicone is applied to the fibers 1700 so as to become interspersed among the fibers 1700 and bind the fibers 1700 together. Heat and pressure are applied to convert the porous adhesive and/or the mixture of the porous adhesive and the fibers 1700 into an NPR material, as described throughout this disclosure. In some implementations, the porous adhesive is cured (e.g., substantially solidified), and then the cured adhesive is converted into the NPR material.

In some implementations, the resulting unibody NPR finger prosthesis 1706 is then stretched (e.g., stretch repeatedly in a stretching machine) to stretch a hinge portion 1708 of the prosthesis. In some implementations, the stretching is carried out in an inert atmosphere, e.g., a nitrogen atmosphere.

In some implementations, the stems 1602 may include an NPR pre-coating layer that improves adhesion between the stems and bone cement, as described elsewhere in this disclosure in the contexts of femoral stems and acetabular cups.

Although the foregoing description in reference to FIGS. 16-17C focuses on finger joint prostheses, other types of prostheses may also include NPR material-containing grommets between a primary body of the prosthesis and bones to which the primary body is affixed, and/or may be formed of biocompatible fibers joined by an NPR binder. For example, toe joint prostheses, elbow joint prostheses, femoral stem prostheses, and other prosthesis types can also be inserted through grommets to maintain homeostasis under varying loads and/or to reduce damage to hinge or stem portions by limiting direct contact between bone and the hinge or stem portions, and/or can be formed of biocompatible fibers join by an NPR binder.

Figure 18:
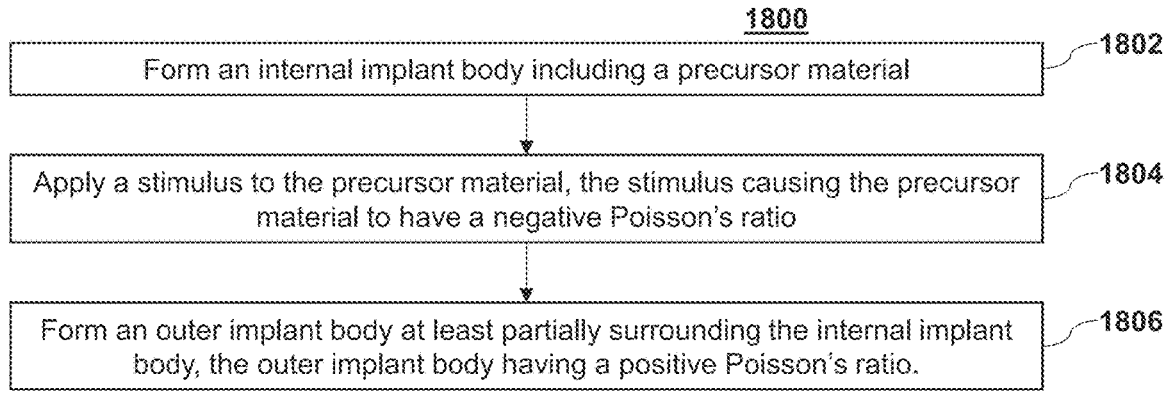
FIGS. 18-20 are diagrams showing example processes.

FIG. 18 shows an example process 1800 in accordance with this disclosure. An internal implant body including a precursor material is formed (1802). A stimulus is applied to the precursor material, the stimulus causing the precursor material to have a negative Poisson's ratio (1804). An outer implant body at least partially surrounding the internal implant body is formed, the outer body having a positive Poisson's ratio (1806).

Figure 19:
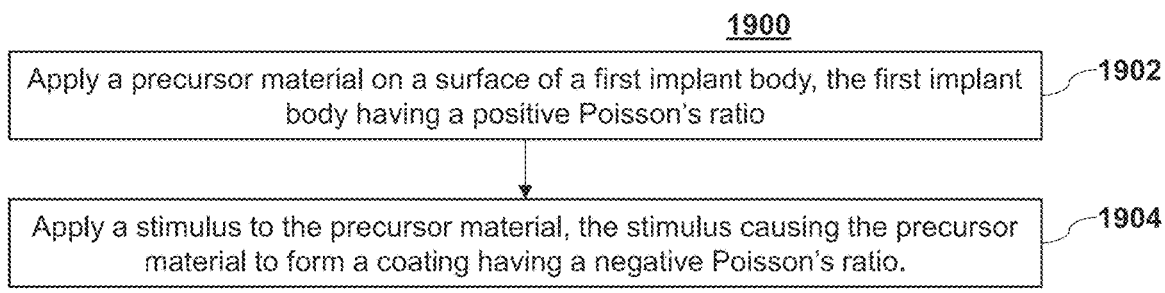

FIG. 19 shows an example process 1900 in accordance with this disclosure. A precursor material is applied on a surface of a first implant body, the first implant body having a positive Poisson's ratio (1902). A stimulus is applied to the precursor material, the stimulus causing the precursor material to form a coating having a negative Poisson's ratio (1904).

Figure 20:
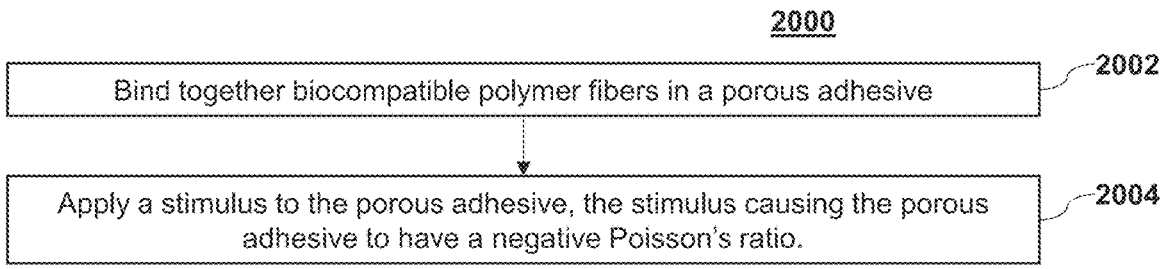

FIG. 20 shows an example process 2000 in accordance with this disclosure. Biocompatible polymer fibers are bound together in a porous adhesive (2002). A stimulus is applied to the porous adhesive, the stimulus causing the porous adhesive to have a negative Poisson's ratio (2004).

Therefore, in accordance with the implementations of this disclosure, medical implants that include NPR materials are described.

Various modifications will be apparent from the foregoing detailed description. For example, structures and processes described in associated with one type of medical implant (e.g., a bone plate, a hip prosthesis component, a finger joint prosthesis component, or a dental implant) may be equally applicable for other types of medical implants, including other types of medical prostheses. Further, features described above in connection with different implementations may, in some cases, be combined in the same implementation. In some instances, the order of the process steps may differ from that described in the particular examples above.

Accordingly, other implementations are also within the scope of the claims.

What is claimed is:

1. A medical implant comprising:
   a first implant body comprising:
   a first portion having a positive Poisson's ratio, and
   an internal second portion embedded in the first portion, the internal second portion having a negative Poisson's ratio; and
   a pre-coating covering at least a portion of an outer surface of the first implant body, the pre-coating having a negative Poisson's ratio.

2. The medical implant of claim 1, wherein the first implant body comprises an inner cup of an acetabular cup.

3. The medical implant of claim 2, wherein the first portion of the inner cup comprises ultra-high-molecular-weight polyethylene.

4. The medical implant of claim 1, wherein the first implant body comprises a prosthetic femoral stem.

5. The medical implant of claim 1, wherein the pre-coating comprises polymethyl methacrylate having a negative Poisson's ratio.

6. The medical implant of claim 1, wherein the pre-coating comprises a bone ingrowth-promoting material having a negative Poisson's ratio.

7. The medical implant of claim 1, wherein the pre-coating has a thickness between 1 mm and 5 mm.

8. The medical implant of claim 1, wherein the first portion of the first implant body comprises a metal capable of forming a native oxide layer, and
   wherein the pre-coating is directly in contact with the metal of the first portion of the first implant body, without the native oxide layer in-between.

9. A method of making a medical implant, the method comprising:
   applying a precursor material on a surface of a first implant body, the first implant body comprising:
   a first portion having a positive Poisson's ratio, and
   an internal second portion embedded in the first portion, the internal second portion having a negative Poisson's ratio; and
   applying a stimulus to the precursor material, the stimulus causing the precursor material to form a coating having a negative Poisson's ratio.

10. The method of claim 9, wherein the stimulus comprises at least one of heat or pressure.

11. The method of claim 9, comprising, prior to applying the precursor material, removing an oxide layer from the surface of the first implant body.

12. The method of claim 9, wherein the coating has a thickness between 1 mm and 5 mm.

13. The method of claim 9, wherein the first implant body comprises an inner cup of an acetabular cup.

14. The method of claim 9, wherein the first implant body comprises a prosthetic femoral stem.

15. The method of claim 9, wherein the precursor material comprises a porous foam.

16. The method of claim 9, wherein the coating comprises polymethyl methacrylate having a negative Poisson's ratio.

17. The method of claim 9, wherein the coating comprises a bone ingrowth-promoting material having a negative Poisson's ratio.

* * * * *